US009330497B2

(12) United States Patent
Byrd et al.

(10) Patent No.: US 9,330,497 B2
(45) Date of Patent: May 3, 2016

(54) USER INTERFACE DEVICES FOR ELECTROPHYSIOLOGY LAB DIAGNOSTIC AND THERAPEUTIC EQUIPMENT

(75) Inventors: Charles Bryan Byrd, Oakdale, MN (US); Eric Betzler, Andover, MN (US); Sandeep Dani, Eden Prairie, MN (US); Israel A. Byrd, Richfield, MN (US); Eric S. Olson, Maplewood, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1281 days.

(21) Appl. No.: 13/208,924

(22) Filed: Aug. 12, 2011

(65) Prior Publication Data

US 2013/0041243 A1 Feb. 14, 2013

(51) Int. Cl.
*G06T 19/00* (2011.01)

(52) U.S. Cl.
CPC ........... *G06T 19/003* (2013.01); *G06T 2210/41* (2013.01)

(58) Field of Classification Search
CPC .... G06T 19/003; G06T 2210/41; G06F 3/041
See application file for complete search history.

(56) References Cited

U.S. PATENT DOCUMENTS

| 3,091,130 | A | 5/1963 | Payerle et al. |
| 3,605,725 | A | 9/1971 | Bentov |
| 3,893,449 | A | 7/1975 | Lee et al. |
| 4,160,508 | A | 7/1979 | Frosch et al. |
| 4,348,556 | A | 9/1982 | Gettig et al. |
| 4,393,728 | A | 7/1983 | Larson et al. |
| 4,543,090 | A | 9/1985 | McCoy |
| 4,758,222 | A | 7/1988 | McCoy |

(Continued)

FOREIGN PATENT DOCUMENTS

| EP | 0151479 | 8/1985 |
| EP | 0904796 | 3/1999 |

(Continued)

OTHER PUBLICATIONS

"Apple Wins Strategic Multitouch and Music Tempo Workout Patents", Patently Apple <URL: http://www.patentlyapple.com/patently-apple/2010/04/apple-wins-strategic-multitouch-music-tempo-workout-patents.html>, Apr. 27, 2010.

(Continued)

*Primary Examiner* — Liliana Cerullo
(74) *Attorney, Agent, or Firm* — Dykema Gossett PLLC

(57) ABSTRACT

In an electrophysiology (EP) lab, a bedside interface device allows an EP physician to directly control various diagnostic and therapeutic systems, including an electro-anatomic mapping system. The bedside interface device can include a computer with wireless communication capability as well as a touch-responsive display panel and voice recognition. The bedside interface device can also be a hand-graspable wireless remote control device that is configured to detect motions or gestures made with the remote control by the physician, allowing the physician to directly interact with the mapping system. The bedside interface device can also be a motion capture camera configured to determine motion patterns of the physician's arms, legs, trunk, face and the like, which are defined in advance to correspond to commands for the mapping system. The bedside interface device may also include voice recognition capabilities to allow a physician to directly issue verbal commands to the mapping system.

22 Claims, 12 Drawing Sheets

(56) References Cited

U.S. PATENT DOCUMENTS

| | | |
|---|---|---|
| 4,784,042 A | 11/1988 | Paynter |
| 4,802,487 A | 2/1989 | Martin |
| 4,884,557 A | 12/1989 | Takehana |
| 4,962,448 A | 10/1990 | DeMaio |
| 4,974,151 A | 11/1990 | Advani et al. |
| 5,078,140 A | 1/1992 | Kwoh |
| 5,107,080 A | 4/1992 | Rosen |
| 5,170,817 A | 12/1992 | Sunderland |
| 5,238,005 A | 8/1993 | Imran |
| 5,298,930 A | 3/1994 | Asakura |
| 5,303,148 A | 4/1994 | Mattson et al. |
| 5,318,525 A | 6/1994 | West |
| 5,339,799 A | 8/1994 | Kami et al. |
| 5,396,266 A | 3/1995 | Brimhall |
| 5,410,638 A | 4/1995 | Colgate et al. |
| 5,441,483 A | 8/1995 | Avitall |
| 5,449,345 A | 9/1995 | Taylor |
| 5,520,644 A | 5/1996 | Imran |
| 5,533,967 A | 7/1996 | Imran |
| 5,545,200 A | 8/1996 | West |
| 5,579,442 A | 11/1996 | Kimoto |
| 5,607,158 A | 3/1997 | Chan |
| 5,607,462 A | 3/1997 | Imran |
| 5,623,582 A | 4/1997 | Rosenberg |
| 5,630,783 A | 5/1997 | Steinberg |
| 5,661,253 A | 8/1997 | Aoki |
| 5,706,827 A | 1/1998 | Ehr |
| 5,784,542 A | 7/1998 | Ohm |
| 5,791,908 A | 8/1998 | Gillio |
| 5,800,178 A | 9/1998 | Gillio |
| 5,807,377 A | 9/1998 | Madhani |
| 5,808,665 A | 9/1998 | Green |
| 5,828,813 A | 10/1998 | Ohm |
| 5,854,622 A | 12/1998 | Brannon |
| 5,861,024 A | 1/1999 | Rashidi |
| 5,876,325 A | 3/1999 | Mizuno et al. |
| 5,897,488 A | 4/1999 | Ueda |
| 5,913,820 A | 6/1999 | Bladen et al. |
| 6,040,758 A | 3/2000 | Sedor |
| 6,063,095 A | 5/2000 | Wang |
| 6,113,395 A | 9/2000 | Hon |
| 6,201,196 B1 | 3/2001 | Wergen |
| 6,233,476 B1 | 5/2001 | Strommer et al. |
| 6,233,504 B1 | 5/2001 | Das et al. |
| 6,290,683 B1 | 9/2001 | Erez |
| 6,348,911 B1 | 2/2002 | Rosenberg |
| 6,358,207 B1 | 3/2002 | Lathbury et al. |
| 6,385,509 B2 | 5/2002 | Das et al. |
| 6,396,232 B2 | 5/2002 | Haanpaa |
| 6,432,112 B2 | 8/2002 | Brock |
| 6,498,944 B1 | 12/2002 | Ben-Haim et al. |
| 6,500,167 B1 | 12/2002 | Webster |
| 6,522,141 B2 | 2/2003 | Debbins et al. |
| 6,540,685 B1 | 4/2003 | Rhoads et al. |
| 6,671,533 B2 | 12/2003 | Chen et al. |
| 6,709,667 B1 | 3/2004 | Lowe |
| 6,785,358 B2 | 8/2004 | Johnson et al. |
| 6,850,252 B1 | 2/2005 | Hoffberg |
| 6,869,390 B2 | 3/2005 | Elliott |
| 6,869,396 B2 | 3/2005 | Belson |
| 6,968,223 B2 | 11/2005 | Hanover |
| 7,016,469 B2 | 3/2006 | Johnson et al. |
| 7,193,521 B2 | 3/2007 | Moberg |
| 7,197,354 B2 | 3/2007 | Sobe |
| 7,199,790 B2 | 4/2007 | Rosenberg |
| 7,247,139 B2 | 7/2007 | Yudkovitch et al. |
| 7,263,397 B2 | 8/2007 | Hauck et al. |
| 7,276,044 B2 | 10/2007 | Ferry |
| 7,386,339 B2 | 6/2008 | Strommer et al. |
| 7,465,288 B2 | 12/2008 | Dudney et al. |
| 7,672,849 B2 | 3/2010 | Yudkovitch et al. |
| 7,698,966 B2 | 4/2010 | Gosselin |
| 7,742,803 B2 | 6/2010 | Viswanathan et al. |
| 7,850,642 B2 | 12/2010 | Moll |
| 7,880,717 B2 | 2/2011 | Berkley et al. |
| 7,945,546 B2 | 5/2011 | Bliss et al. |
| 7,963,288 B2 | 6/2011 | Rosenberg et al. |
| 8,164,573 B2 | 4/2012 | DaCosta et al. |
| 8,317,744 B2 | 11/2012 | Kirschenman |
| 8,317,745 B2 | 11/2012 | Kirschenman |
| 8,332,072 B1 | 12/2012 | Schaible et al. |
| 8,390,438 B2 | 3/2013 | Olson |
| 8,416,203 B2 | 4/2013 | Tsui |
| 8,560,118 B2 | 10/2013 | Greer et al. |
| 8,926,511 B2 | 1/2015 | Bar-Tar |
| 2001/0018591 A1 | 8/2001 | Brock |
| 2001/0025183 A1 | 9/2001 | Shahidi |
| 2002/0068868 A1 | 6/2002 | Thompson et al. |
| 2002/0072704 A1 | 6/2002 | Mansouri-Ruiz |
| 2002/0087048 A1 | 7/2002 | Brock |
| 2002/0184055 A1 | 12/2002 | Naghavi et al. |
| 2003/0018232 A1 | 1/2003 | Elliott |
| 2003/0050733 A1 | 3/2003 | Wang et al. |
| 2003/0114962 A1 | 6/2003 | Niemeyer |
| 2003/0121382 A1 | 7/2003 | Morson |
| 2004/0050247 A1 | 3/2004 | Topping |
| 2004/0068173 A1 | 4/2004 | Viswanathan |
| 2004/0133189 A1 | 7/2004 | Sakurai |
| 2004/0138530 A1 | 7/2004 | Kawai et al. |
| 2004/0146388 A1 | 7/2004 | Khajepour et al. |
| 2004/0193239 A1 | 9/2004 | Falwell et al. |
| 2004/0223636 A1 | 11/2004 | Edic |
| 2004/0243147 A1 | 12/2004 | Lipow |
| 2005/0038333 A1 | 2/2005 | Sra |
| 2005/0075538 A1 | 4/2005 | Banik |
| 2005/0172405 A1 | 8/2005 | Menkedick et al. |
| 2005/0203382 A1 | 9/2005 | Govari |
| 2005/0222554 A1 | 10/2005 | Wallace |
| 2005/0234293 A1 | 10/2005 | Yamamoto et al. |
| 2005/0234320 A1 | 10/2005 | Balasubramanian |
| 2006/0052664 A1 | 3/2006 | Julian |
| 2006/0089637 A1 | 4/2006 | Werneth et al. |
| 2006/0137476 A1 | 6/2006 | Bull |
| 2006/0155321 A1 | 7/2006 | Bressler et al. |
| 2006/0276775 A1* | 12/2006 | Rosenberg et al. ............... 606/1 |
| 2006/0293643 A1 | 12/2006 | Wallace |
| 2007/0016008 A1 | 1/2007 | Schoenefeld |
| 2007/0022384 A1 | 1/2007 | Abbott et al. |
| 2007/0043338 A1 | 2/2007 | Moll et al. |
| 2007/0060833 A1 | 3/2007 | Hauck |
| 2007/0073137 A1 | 3/2007 | Schoenefeld |
| 2007/0100254 A1 | 5/2007 | Murakami et al. |
| 2007/0120512 A1 | 5/2007 | Albu-Schaffer |
| 2007/0135803 A1 | 6/2007 | Belson |
| 2007/0142726 A1 | 6/2007 | Carney |
| 2007/0172803 A1 | 7/2007 | Hannaford et al. |
| 2007/0185404 A1 | 8/2007 | Hauck et al. |
| 2007/0185485 A1 | 8/2007 | Hauck |
| 2007/0185486 A1 | 8/2007 | Hauck |
| 2007/0197896 A1 | 8/2007 | Moll et al. |
| 2007/0197939 A1 | 8/2007 | Wallace |
| 2007/0198008 A1 | 8/2007 | Hauck et al. |
| 2007/0233044 A1 | 10/2007 | Wallace |
| 2007/0233045 A1 | 10/2007 | Weitzner |
| 2007/0270685 A1 | 11/2007 | Kang |
| 2007/0276214 A1 | 11/2007 | Dachille |
| 2007/0298877 A1 | 12/2007 | Rosenberg et al. |
| 2008/0009791 A1 | 1/2008 | Cohen |
| 2008/0013809 A1 | 1/2008 | Zhu |
| 2008/0112842 A1 | 5/2008 | Edwards |
| 2008/0201847 A1 | 8/2008 | Menkedick |
| 2008/0312536 A1 | 12/2008 | Dala-Krishna |
| 2009/0012533 A1 | 1/2009 | Barbagli et al. |
| 2009/0033623 A1 | 2/2009 | Lin |
| 2009/0061928 A1 | 3/2009 | Lee et al. |
| 2009/0123111 A1 | 5/2009 | Udd |
| 2009/0137952 A1 | 5/2009 | Ramamurthy et al. |
| 2009/0177454 A1 | 7/2009 | Bronstein |
| 2009/0192519 A1 | 7/2009 | Omori et al. |
| 2009/0195514 A1 | 8/2009 | Glynn et al. |
| 2009/0247993 A1 | 10/2009 | Kirschenman et al. |
| 2009/0264156 A1 | 10/2009 | Burghardt et al. |
| 2009/0322697 A1 | 12/2009 | Cao |
| 2010/0066676 A1 | 3/2010 | Kramer |

(56) References Cited

U.S. PATENT DOCUMENTS

| | | |
|---|---|---|
| 2010/0073150 A1 | 3/2010 | Olson |
| 2010/0079386 A1 | 4/2010 | Scott et al. |
| 2010/0082039 A1 | 4/2010 | Mohr et al. |
| 2010/0103127 A1 | 4/2010 | Park et al. |
| 2010/0256558 A1 | 10/2010 | Olson et al. |
| 2010/0268067 A1 | 10/2010 | Razzaque |
| 2010/0314031 A1 | 12/2010 | Heideman et al. |
| 2011/0040547 A1* | 2/2011 | Gerber et al. .................. 703/11 |
| 2011/0128555 A1 | 6/2011 | Rotschild et al. |
| 2011/0137156 A1 | 6/2011 | Razzaque et al. |
| 2011/0152882 A1 | 6/2011 | Wenderow et al. |
| 2011/0289441 A1* | 11/2011 | Venon et al. .................. 715/771 |
| 2011/0306986 A1 | 12/2011 | Lee et al. |
| 2012/0071891 A1 | 3/2012 | Itkowitz |
| 2012/0133601 A1* | 5/2012 | Marshall et al. ............. 345/173 |
| 2012/0277663 A1 | 11/2012 | Millman et al. |
| 2013/0006268 A1 | 1/2013 | Swarup et al. |
| 2013/0154913 A1 | 6/2013 | Genc |
| 2013/0165854 A1 | 6/2013 | Sandhu et al. |
| 2013/0176220 A1 | 7/2013 | Merschon et al. |
| 2013/0179162 A1 | 7/2013 | Merschon et al. |

FOREIGN PATENT DOCUMENTS

| | | |
|---|---|---|
| GB | 2211280 | 6/1989 |
| GB | 2397177 | 7/2007 |
| JP | S60221280 | 11/1985 |
| JP | H06344285 | 12/1994 |
| JP | H8-280709 | 10/1996 |
| JP | H10216238 | 8/1998 |
| JP | 2003024336 | 1/2003 |
| JP | 2007325936 | 12/2007 |
| WO | 9320535 | 10/1993 |
| WO | 96/39944 | 12/1996 |
| WO | 03049596 | 6/2003 |
| WO | 2006/120666 | 11/2006 |
| WO | 2007/088208 | 8/2007 |
| WO | 2007/098494 | 8/2007 |
| WO | 2007/120329 | 10/2007 |
| WO | 2007136803 | 11/2007 |
| WO | 2007/146325 | 12/2007 |
| WO | 2007143859 | 12/2007 |
| WO | 2008045831 | 4/2008 |
| WO | 2008101228 | 8/2008 |
| WO | 2008103212 | 8/2008 |
| WO | 2009/120992 | 10/2009 |
| WO | 2009120940 | 10/2009 |
| WO | 2009120992 | 10/2009 |
| WO | 2010025338 | 3/2010 |
| WO | WO 2010-059179 | 5/2010 |
| WO | 2010068783 | 6/2010 |
| WO | 2010107916 | 9/2010 |

OTHER PUBLICATIONS

"Polaris Family of Optical Tracking Systems, Polaris Vicra & Spectra—Optical Measurement Systems for Medical", Northern Digital Inc. <URL: http://www.ndigital.com/medical/polarisfamily.php?act=print>, Feb. 20, 2012.

"The Aurora Electromagnetic Tracking System, Aurora Electromagnetic Measurement System—3D Trackinhg for Medical Guidance", Northern Digital Inc. <URL: http://www.ndigital.com/medical/aurora.pho?act=print>, Feb. 20, 2013.

Labelle, Kathryn, "Evaluation of Kinect Joint Tracking for Clinical and In-Home Stroke Rehabilitation Tools", <http://netscale.cse.nd.edu/twiki/pub/Edu/KinectRehabilitation/Eval_of_Kinect_for_Rehab.pdf>, Dec. 2011.

Padoy, Nicolas et al., "Needle Insertion Revisted (tele-surgery in depth), (online)", The John Hopkins University <URL: http://www.youtube.com/watch?v=YsY_A0kLh-g>, Jan. 2011.

Japanese Office action (translated by foreign associate) dated Oct. 21, 2014.

Emotiv EPOC Software Development Kit—EPOC neuroheadset [online] [retrieved on Aug. 11, 2011]. Retrieved from the internet: <URL: http://www.emotiv.com/store/hardware/epoc-bci/epoc-neuroheadset/>.

Emotiv—Brain Computer Interface Technology [online] [retrieved on Aug. 11, 2011]. Retrieved from the internet: <URL: http://www.emotiv.com>.

Wii Remote—Wikipedia, the free encyclopedia [online] [retrieved on Aug. 3, 2011]. Retrieved from the internet: <URL: http://en.wikipedia.org/wiki/Wii_Remote>.

About the Kinect for Windows SDK—Microsoft Research [online] [retrieved on Aug. 5, 2011]. Retrieved from the internet: <URL: http://research.microsoft.com/en-us/um/redmond/projects/kinectsdk/about.aspx>.

Kinect—Wikipedia, the free encyclopedia [online] [retrieved on Aug. 3, 2011]. Retrieved from the internet: <URL: http://en.wikipedia.org/wiki/Kinect>.

"International Search Report & Written Opinion", PCT/US2012/031008 Jul. 20, 2012.

Author: Title: International Search Report and Written Opinion Citation: PCT/US2011/030764 Publication Date: Jun. 15, 2011.

Ghobadi, et al. "Real Time Hand Based Robot Control Using Multimodal Images", IAENG International Journal of Computer Sciences, 35:4, IJCS_35_4_08: Nov. 20, 2008. 6 pgs.

Robot.pdf (Robot—Definition Robot at Dictionary.com, Oct. 27, 2015, http://dictionary.reference.com/browse/robot, pp. 1-5).

Title: Supplemental European Search Report Citation: EP Application No. 11763450.1 Publication Date: Oct. 29, 2014 9 pages.

Title: International Search Report Citation: PCT Application No. PCT/US2011/030656 Publication Date: Jun. 13, 2011 8 pages.

Title: Supplemental European Search Report Citation: EP Application No. 09726364.4 Publication Date: Jan. 22, 2013 7 pages.

Title: Supplemental European Search Report Citation: EP Application No. 09723739.0 Publication Date: Jul. 10, 2012 6 pages.

Title: Supplemental European Search Report Citation: EP Application No. 09724550.0 Publication Date: Jul. 10, 2012 6 pages.

Title: International Search Report Citation: PCT Application No. PCT/US2009/058121 Publication Date: Nov. 19, 2009 2 pages.

Title: International Search Report Citation: PCT Application No. PCT/US2009/038536 Publication Date: May 28, 2009 2 pages.

Title: International Search Report Citation: PCT Application No. PCT/US2009/038534 Publication Date: May 27, 2009 2 pages.

Title: International Search Report Citation: PCT Application No. PCT/US2009/038597 Publication Date: May 18, 2009 2 pages.

An International Search Report for PCT Application No. PCT/US2009/069712, dated Feb. 25, 2010, 10 pgs.

A Supplementary European Search Report for EP Application No. 09725131.8, dated Feb. 20, 2013. 7 pgs.

Title: International Search Report Citation: PCT Application No. PCT/US2009/038525 Publication Date: May 27, 2009 2 pages.

Title: International Search Report Citation: PCT Application No. PCT/US2009/038531 Publication Date: May 19, 2009 3 pages.

Title: International Search Report Citation: PCT Application No. PCT/US2009/038533 Publication Date: Jun. 17, 2009 2 pages.

Title: International Search Report Citation: PCT Application No. PCT/US2009/038618 Publication Date: May 22, 2009 2 pages.

A Supplementary European Search Report for EP Application No. 11763410.5, dated Jun. 10, 2015, 1 pg.

* cited by examiner

USER INTERFACE DEVICES FOR ELECTROPHYSIOLOGY LAB DIAGNOSTIC AND THERAPEUTIC EQUIPMENT

BACKGROUND OF THE INVENTION a. Field of the Invention

The instant disclosure relates generally to electrophysiology lab integration, and more particularly to user interfaces and devices therefore for electrophysiology lab diagnostic and therapeutic equipment.

b. Background Art

It is known to provide an electrophysiology lab in a medical facility. Such a lab may have use of a wide variety of diagnostic and therapeutic equipment useful in rendering medical service to a patient, such as imaging systems (e.g., fluoroscopy, intracardiac echocardiography, etc.), an electro-anatomic visualization, mapping and navigation system, ablation energy sources (e.g., radio frequency (RF) ablation generator), a recording system (e.g., for ECG, cardiac signals, etc.), a cardiac stimulator and the like. In a typical configuration, as seen by reference to FIG. 1, a procedure room 10 (i.e., a sterile environment) may have an associated control area or room 12, which is commonly outfitted with one or more control stations $14_1, 14_2, \ldots 14_n$ that are operated by one or more control technicians. Each control station may include a respective display monitor, keyboard and mouse for use by the technician. Depending on the lab setup, the control station(s) may be across the room, or outside of the procedure room 10 completely, perhaps configured with a common window to allow the technician(s) to observe the procedure room through the window. These control station(s) allow access to and may be used to control the diagnostic and therapeutic equipment mentioned above.

In conventional practice, an electrophysiology (EP) physician 16 is scrubbed into a sterile procedure and typically manipulates one or more catheters (not shown) in a sterile drape covered body of the patient 18. The physician's sterile gloved hands are typically engaged with the catheter handle and shaft next to the patient and he or she is therefore unable to directly make changes himself to any of the EP systems. The procedure room 10 typically includes one or more monitors (e.g., an integrated multi-display monitor 20 is shown) arranged so that the physician 16 can see the monitor 20 on which is displayed various patient information being produced by the diagnostic and therapeutic equipment mentioned above. In FIG. 1, multiple applications, for example, an electro-anatomic mapping application (e.g., EnSite Velocity™) and an EP signal acquisition and recording application, direct a visual output to a respective display area of monitor 20. When changes to an application are needed, the physician 16 verbalizes such commands to the control technicians in the control area/room 12 who are working at the various control stations $14_1, 14_2, \ldots 14_n$. The multiple technicians at multiple control stations use multiple keyboard/mouse sets to control the multiple applications. The verbal commands between the physician and the technician occur throughout the procedure.

For example, the EP physician 16 can verbally communicate (i.e., to the control technician—a mapping system operator) the desired view of the map to be displayed, when to collect points, when to separate anatomic locations, and other details of creating and viewing an anatomic map. The EP physician 16 can also communicate which signal traces to show, the desired amplitude, when to drop a lesion marker, and when to record a segment, to name a few. Where the technician is in a separate room, communication can be facilitated using radio.

While some commands are straightforward, for example, "LAO View", "record that" and "stop pacing", other commands are not as easy to clearly communicate. For example, how much rotation of a model the command "rotate a little to the right" means can be different as between the physician and the technician. This type of command therefore involves a question of degree. Also, depending on the physician-technician relationship, other requests related to the mapping system views and setup can be misinterpreted. For example, a request to "rotate right" may mean to rotate the model right (i.e., rotate view left) when originating from one physician but can alternatively mean rotate view right (i.e., rotate model left) when coming from another physician. This type of command therefore involves physician-technician agreement as to convention. Furthermore, implementation of requests for event markers, segment recordings, lesion markers and the like can be delayed by the time it takes the technician to hear, understand and act on a physician's command. Ambient discussions and/or equipment noise in and around the EP lab can increase this delay.

There is therefore a need for improvements in EP lab integration that minimize or eliminate one or more problems are set forth above.

BRIEF SUMMARY OF THE INVENTION

One advantage of the methods and apparatuses described, depicted and claimed herein is that they provide an EP physician with the capability of directly controlling an EP diagnostic or therapeutic system, such as an electro-anatomic mapping system. This capability eliminates the need for the physician to first communicate his/her wishes to a control technician, who in turn must hear, interpret and act on the physician's command. The improved control paradigm results in reduced times for medical procedures.

A device for allowing a user to control an electro-anatomic mapping system includes an electronic control unit (ECU) and input means, using the ECU, for acquiring a user input with respect to a view of an anatomical model of at least a portion of a body of a patient. The user input is selected from the group comprising a user touch, a user multi-touch, a user gesture, a verbal command, a motion pattern of a user-controlled object, a user motion pattern and a user electroencephalogram. The ECU is configured to communicate the acquired input to the mapping system for further processing.

In an embodiment, the acquired user input can correspond to any of a variety of mapping systems commands, for example only at least one of: (1) creating a map with respect to the view; (2) collecting points with respect to the view; (3) segmenting regions by anatomy with respect to the view; (4) rotating the view; (5) enlarging or reducing a portion of the view; (6) panning the view; (7) selecting one of a plurality of maps for the view; (8) selecting a signal trace; (9) adjusting a signal amplitude; (10) adjusting a sweep speed; (11) recording a segment; (12) placing an event marker; (13) placing a lesion marker with respect to the view; (14) activating a replay feature of a stored, temporally varying physiologic parameter; and (15) activating a replay of a stored video clip.

In an embodiment, the input means includes a touch-responsive display panel coupled to the ECU. The input means also includes user interface logic (executed by the ECU) configured to display a user interface on the touch-responsive display panel. The user interface logic is further configured to allow a user to interact with the touch-responsive panel for acquiring the above-mentioned user input with respect to the anatomical model. The user interface in combination with the touch-panel allows the user to provide input by way of touch, multi-touch, and gesture. In a further embodiment, the device further includes voice recognition logic configured to recognize a set of predefined verbal commands spoken by the user (e.g., the physician). In a still further embodiment, the device includes wireless communications functionality, improving portability of the device within a procedure room or the control room. In a still further embodiment, the user interface logic is configured to present a plurality of application-specific user interfaces associated with a plurality of different diagnostic or therapeutic systems. Through this capability, the user can rapidly switch between application-specific user interfaces (e.g., such as that for an electro-anatomic mapping system, an EP recording system, an ultrasound imaging system, a cardiac stimulator, etc.), while remaining bedside of the patient, and without needing to communicate via a control technician.

In another embodiment, the input means includes a remote control having a handle configured to be grasped by the user. The remote control includes logic configured to acquire the above-mentioned user input. The user input may include user-controlled motion patterns of the remote control, as well as user key-presses on the remote control. The device is also configured to communicate the acquired user input to the mapping system.

In yet another embodiment, the input means includes a motion capture apparatus configured to acquire imaging of movements of the user. The device includes logic configured to identify a motion pattern using the acquired imaging from the motion capture apparatus. The logic is further configured to produce a command, based on the identified motion pattern, and communicate the command to the electro-anatomic mapping system for further processing. The motion capture apparatus provides the capability of receiving input by way of physician gestures (e.g., hand, arm, leg, trunk, facial, etc.). In a further embodiment, the device further includes voice recognition logic configured to identify verbal commands spoken by the user.

Corresponding methods are also presented.

The foregoing and other aspects, features, details, utilities, and advantages of the present disclosure will be apparent from reading the following description and claims, and from reviewing the accompanying drawings.

DETAILED DESCRIPTION OF THE INVENTION

Figure 1:
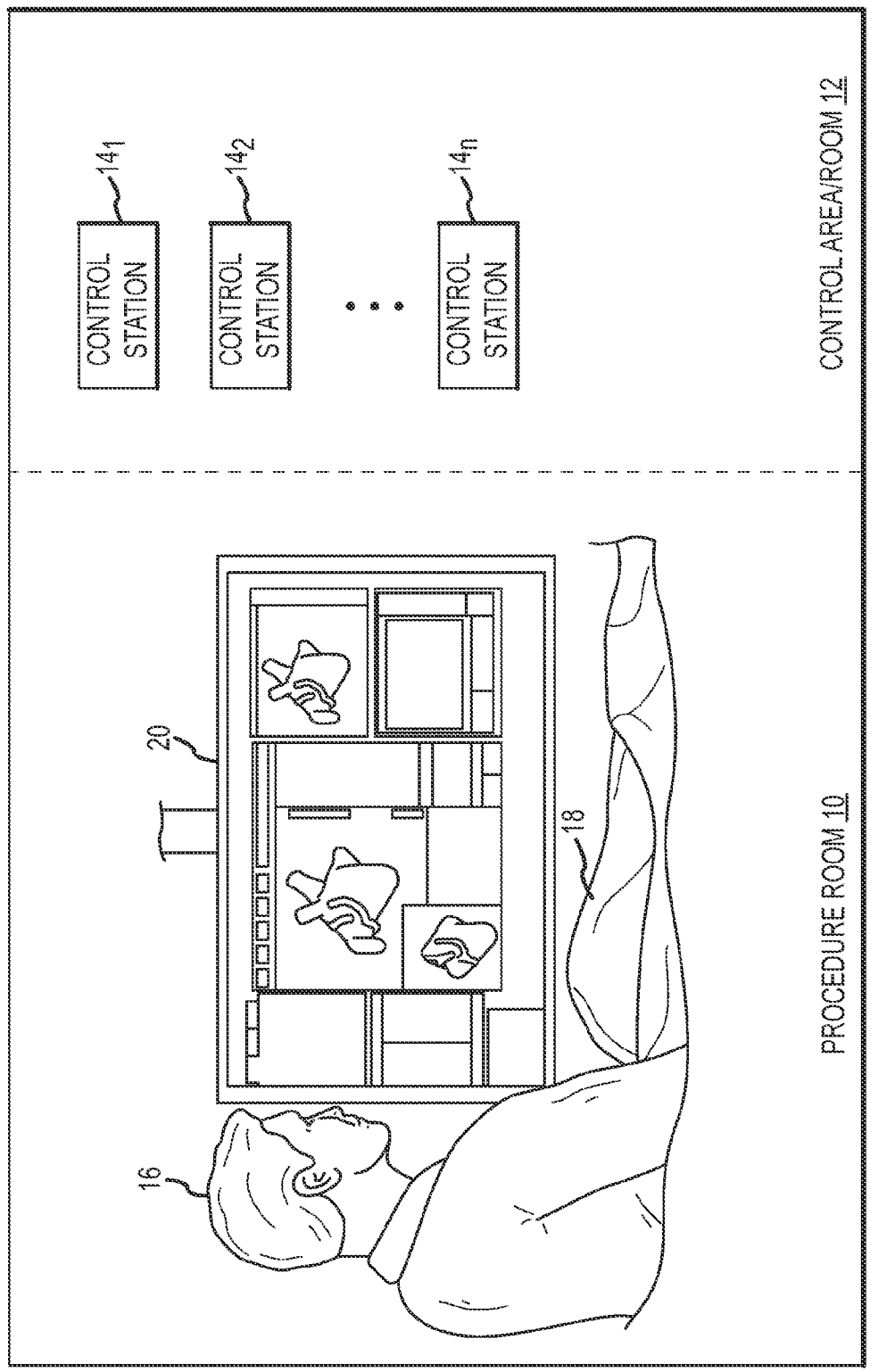
FIG. 1 is a block diagram view of a conventional electrophysiology lab having a sterile procedure room and an associated control room.
Figure 2:
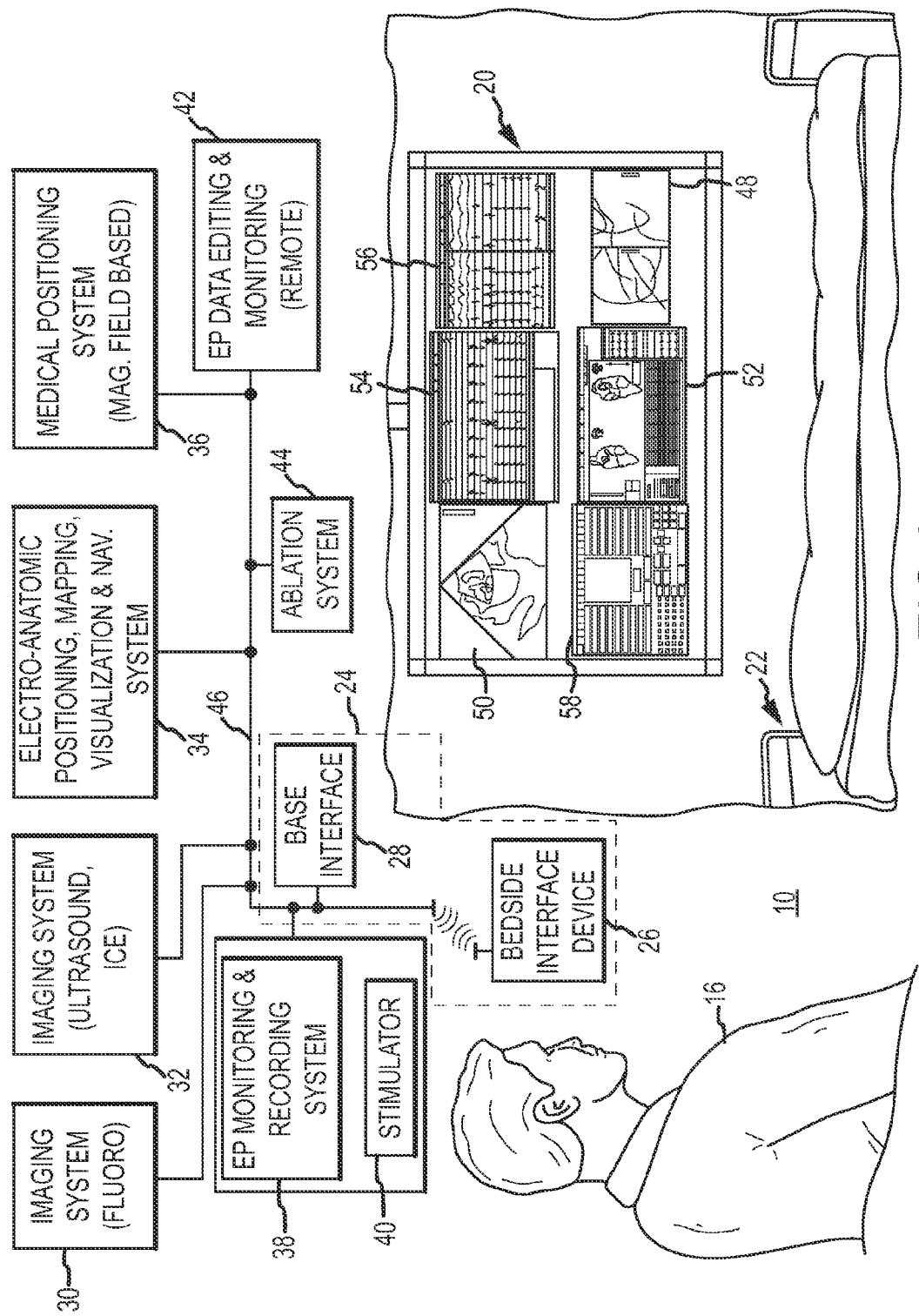
FIG. 2 is a block diagram view of an embodiment of an electrophysiology lab having a bedside interface device for controlling diagnostic and therapeutic equipment.

Referring now to the drawings wherein like reference numerals are used to identify identical or similar components in the various views, FIG. 2 is a diagrammatic overview of an electrophysiology (EP) laboratory in which embodiments of the present invention may be used. FIG. 2 shows a sterile procedure room 10 where an EP physician 16 is set to perform one or more diagnostic and/or therapeutic procedures. It should be understood that the separate control area/room 12 of FIG. 1 (not shown in FIG. 2) may continue to be used in conjunction with the bedside interface device to be described below. FIG. 2 also shows multi-display monitor 20 as well as a procedure table or bed 22. While procedure room 10 may include multiple, individual monitors, monitor 20 may be a multi-display monitor configured to display a plurality of different input channels in respective display areas on the monitor. In an embodiment, the monitor 20 may be a commercially available product sold under the trade designation VantageView™ from St. Jude Medical, Inc. of St. Paul, Minn., USA, which can have a 3840×2160 Quad-HD screen resolution with the flexibility to accept up to sixteen (16) digital or analog image inputs while displaying up to eight (8) images on one screen at one time. The procedure table 22, which may be of conventional construction, is configured to receive a patient (not shown) on whom diagnostic and/or therapeutic procedure(s) are to be performed.

FIG. 2 further shows means or apparatus 24 for facilitating physician interaction with one or more diagnostic and/or therapeutic systems. Means or apparatus 24 includes a bedside interface device 26 and optionally one or more base interfaces 28. Means or apparatus 24 provides the mechanism for the EP physician 16 to directly interact with such systems without the need for the intermediate step of verbalizing commands to a control technician, as described in connection with FIG. 1. In this regard, bedside interface device 26 is configured to present a user interface or other input logic with which the user (e.g., the EP physician 16) can directly interact or from which an input can be acquired. In multiple embodiments, various modes of interaction are presented, such as interaction via a user touch, a user multi-touch, a user gesture, a verbal command, a motion pattern of a user-controlled device, a user motion pattern and a user electroencephalogram. In addition, bedside interface device 26 can be configured to communicate with one or more of the diagnostic/therapeutic systems either wirelessly (as shown) or via a wired connection (not shown).

The base interface 28 is configured to interpret and/or facilitate directing the input acquired by the bedside interface device 26 to the appropriate one or more diagnostic and/or therapeutic systems (e.g., an electro-anatomic mapping system). In an embodiment, base interface 28 is centralized (as shown), wherein all communications with bedside device 26 occur through base interface 28. In a further embodiment, base interface 28 may be functionally distributed, wherein interface functions are located within each diagnostic or therapeutic system. In a still further embodiment, communications between bedside interface 26 and certain ones of the diagnostic/therapeutic systems can be centralized, while communications with other ones of the diagnostic/therapeutic systems can occur directly (i.e., separately).

The means or apparatus 24 addresses a number of the shortcomings of the conventional practice as described in the Background. For example, means or apparatus 24 allows the EP physician 16 to directly input levels of degree, for example, how much to rotate a view, as opposed to trying to verbally communicate "how much" to a control technician. Further, the use of means or apparatus 24 avoids the potential confusion that can sometimes occur between the EP physician and the control technician as to convention (i.e., does "rotate right" mean rotate the view or the model?). In addition, the use of means or apparatus 24 reduces or eliminates the inherent time delay between the time when the EP physician verbally issues a command and the time when the command is understood and acted upon by the technician.

With continued reference to FIG. 2, the physician 16 will typically have access to a plurality of diagnostic and/or therapeutic systems in order to perform one or more medical procedures. In the illustrative embodiment, the physician 16 may have access to a first imaging system, such as a fluoroscopic imaging system 30, a second imaging system, such as an intracardiac ultrasound or echocardiography (ICE) imaging system 32, an electro-anatomic positioning, mapping, and visualization system 34, a further positioning system, such as a medical positioning system (magnetic-field based) 36, a patient data (electrophysiological (EP) data) monitoring and recording system 38, a cardiac stimulator 40, an EP data editing/monitoring system 42 and an ablation system 44. FIG. 2 schematically shows a communication mechanism 46 which facilitates communication between and among the various systems described above. It should be understood, however, that the communications mechanism 46 may not necessarily function to enable communications between each and every system shown.

The fluoroscopic imaging system 30 may comprise conventional apparatus known in the art, for example, single plane or bi-plane configurations. A display area 48 that is shown on monitor 20 corresponds to the display output of fluoroscopic imaging system 30.

The intracardiac ultrasound and/or intracardiac echocardiography (ICE) imaging system 32 may also comprise conventional apparatus known in the art. For example, in one embodiment, the system 32 may comprise a commercial system available under the trade designation ViewMate™ Z intracardiac ultrasound system compatible with a ViewFlex™ PLUS intracardiac echocardiography (ICE) catheter, from St. Jude Medical, Inc. of St. Paul, Minn., USA. The system 32 is configured to provide real-time image guidance and visualization, for example, of the cardiac anatomy. Such high fidelity images can be used to help direct diagnosis or therapy during complex electrophysiology procedures. A display area 50 that is shown on monitor 20 corresponds to the display output of the ultrasound imaging system 32.

The system 34 is configured to provide many advanced features, such as visualization, mapping, navigation support and positioning (i.e., determine a position and orientation (P&O) of a sensor-equipped medical device, for example, a P&O of a distal tip portion of a catheter). Such functionality can be provided as part of a larger visualization, mapping and navigation system, for example, an ENSITE VELOCITY™ cardiac electro-anatomic mapping system running a version of EnSite NavX™ navigation and visualization technology software commercially available from St. Jude Medical, Inc., of St. Paul, Minn. and as also seen generally by reference to U.S. Pat. No. 7,263,397 entitled "METHOD AND APPARATUS FOR CATHETER NAVIGATION AND LOCATION AND MAPPING IN THE HEART" to Hauck et al., or U.S. Patent Publication No. 2007/0060833 A1 to Hauck entitled "METHOD OF SCALING NAVIGATION SIGNALS TO ACCOUNT FOR IMPEDANCE DRIFT IN TISSUE", both owned by the common assignee of the present invention, and both hereby incorporated by reference in their entireties as though fully set forth herein. System 34 can be configured to perform further advanced functions, such as motion compensation and adjustment functions. Motion compensation may include, for example, compensation for respiration-induced patient body movement, as described in copending U.S. patent application Ser. No. 12/980,515, entitled "DYNAMIC ADAPTIVE RESPIRATION COMPENSATION WITH AUTOMATIC GAIN CONTROL", which is hereby incorporated by reference in its entirety as though fully set forth herein. System 34 can be used in connection with or for various medical procedures, for example, EP studies or cardiac ablation procedures.

System 34 is further configured to generate and display three dimensional (3D) cardiac chamber geometries or models, display activation timing and voltage data to identify arrhythmias, and to generally facilitate guidance of catheter movement in the body of the patient. For example, a display area 52 that is shown on monitor 20 corresponds to the display output of system 34, can be viewed by physician 16 during a procedure, which can visually communicate information of interest or need to the physician. The display area 52 in FIG. 2 shows a 3D cardiac model, which, as will be described below in greater detail, may be modified (i.e., rotated, zoomed, etc.) pursuant to commands given directly by physician 16 via the bedside interface device 26.

System 36 is configured to provide positioning information with respect to suitably configured medical devices (i.e., those including a positioning sensor). System 36 may use, at least in part, a magnetic field based localization technology, comprising conventional apparatus known in the art, for example, as seen by reference to U.S. Pat. No. 7,386,339 entitled "MEDICAL IMAGING AND NAVIGATION SYSTEM", U.S. Pat. No. 6,233,476 entitled "MEDICAL POSITIONING SYSTEM", and U.S. Pat. No. 7,197,354 entitled "SYSTEM FOR DETERMINING THE POSITION AND ORIENTATION OF A CATHETER", all of which are hereby incorporated by reference in their entirety as though fully set forth herein. System 36 may comprise a gMPS™ medical positioning system commercially offered by MediGuide Ltd. of Haifa, Israel and now owned by St. Jude Medical, Inc. of St. Paul, Minn., USA. System 36 may alternatively comprise variants, which employ magnetic field generator operation, at least in part, such as a combination magnetic field and current field-based system such as the CARTO™ 3 System available from Biosense Webster, and as generally shown with reference to one or more of U.S. Pat. Nos. 6,498,944 entitled "Intrabody Measurement," 6,788,967 entitled "Medical Diagnosis, Treatment and Imaging Systems," and 6,690,963 entitled "System and Method for Determining the Location and Orientation of an Invasive Medical Instrument," the entire disclosures of which are incorporated herein by reference as though fully set forth herein.

EP monitoring and recording system 38 is configured to receive, digitize, display and store electrocardiograms, invasive blood pressure waveforms, marker channels, and ablation data. System 38 may comprise conventional apparatus known in the art. In one embodiment, system 38 may comprise a commercially available product sold under the trade designation EP-WorkMate™ from St. Jude Medical, Inc. of St. Paul, Minn., USA. The system 38 can be configured to record a large number of intracardiac channels, may be further configured with an integrated cardiac stimulator (shown in FIG. 2 as stimulator 40), as well as offering storage and retrieval capabilities of an extensive database of patient information. Display areas 54, 56 shown on monitor 20 correspond to the display output of EP monitoring and recording system 38.

Cardiac stimulator 40 is configured to provide electrical stimulation of the heart during EP studies. Stimulator 40 can be provided in either a stand-alone configuration, or can be integrated with EP monitoring and recording system 38, as shown in FIG. 2. Stimulator 40 is configured to allow the user to initiate or terminate tachy-arrhythmias manually or automatically using preprogrammed modes of operation. Stimulator 40 may comprise conventional apparatus known in the art. In an embodiment, stimulator 40 can comprise a commercially available cardiac stimulator sold under the trade designation EP-4™ available from St. Jude Medical, Inc. of St. Paul, Minn., USA. The display area 58 shown on monitor 20 corresponds to the display output of the cardiac stimulator 40.

EP data editing/monitoring system 42 is configured to allow editing and monitoring of patient data (EP data), as well as charting, analysis, and other functions. System 42 can be configured for connection to EP data recording system 38 for real-time patient charting, physiological monitoring, and data analysis during EP studies/procedures. System 42 may comprise conventional apparatus known in the art. In an embodiment, system 42 may comprise a commercially available product sold under the trade designation EP-NurseMate™ available from St. Jude Medical, Inc. of St. Paul, Minn., USA.

To the extent the medical procedure involves tissue ablation (e.g., cardiac tissue ablation), ablation system 44 can be provided. The ablation system 44 may be configured with various types of ablation energy sources that can be used in or by a catheter, such as radio-frequency (RF), ultrasound (e.g. acoustic/ultrasound or HIFU), laser, microwave, cryogenic, chemical, photo-chemical or other energy used (or combinations and/or hybrids thereof) for performing ablative procedures. RF ablation embodiments may and typically will include other structure(s) not shown in FIG. 2, such as one or more body surface electrodes (skin patches) for application onto the body of a patient (e.g., an RF dispersive indifferent electrode/patch), an irrigation fluid source (gravity feed or pump), and an RF ablation generator (e.g., such as a commercially available unit sold under the model number IBI-1500T RF Cardiac Ablation Generator, available from St. Jude Medical, Inc.).

Figure 3A:
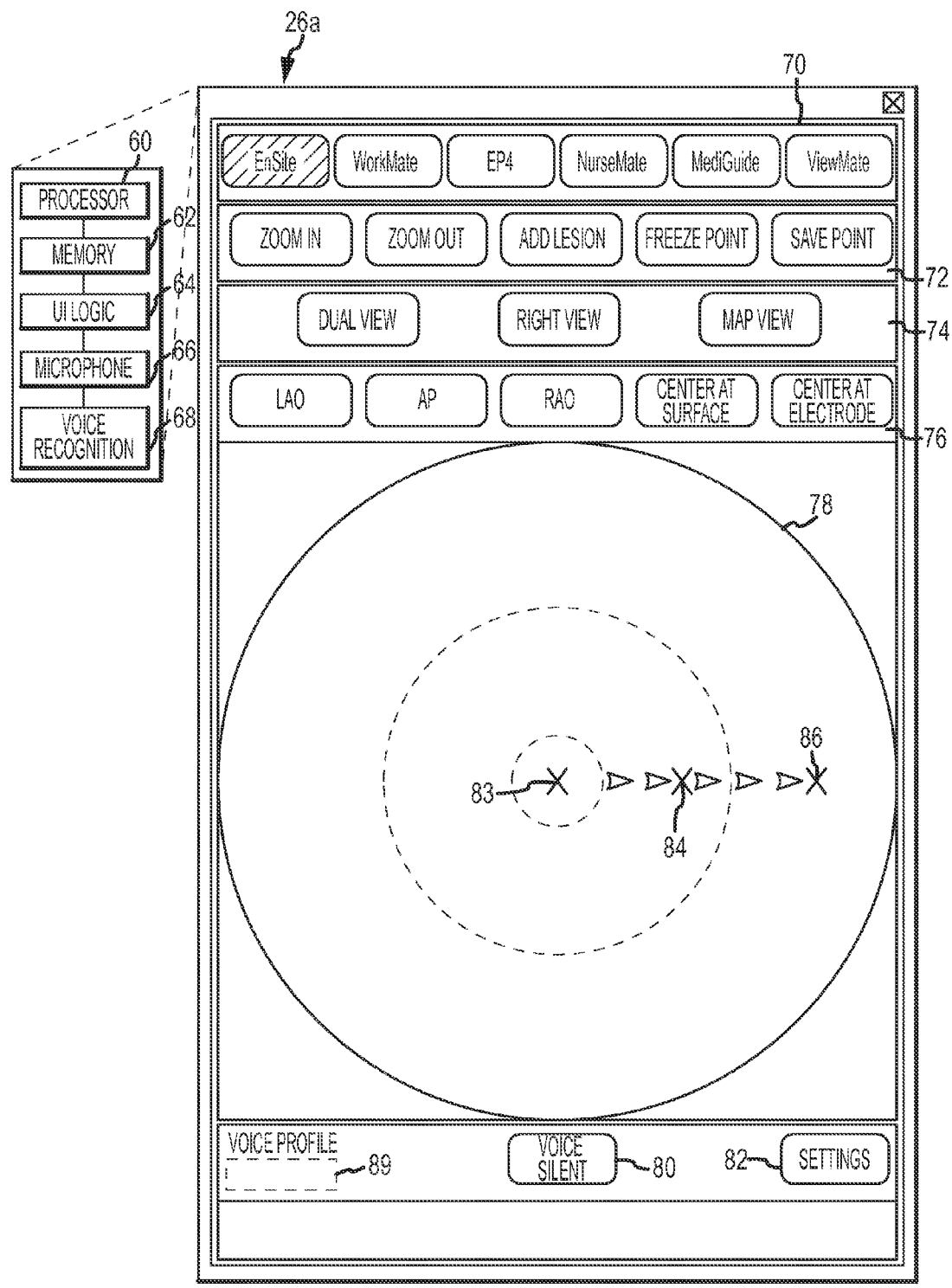
FIG. 3A is a plan view of a first embodiment of a bedside interface device comprising a touch panel computer, suitable for use in the EP lab of FIG. 2, and showing a first application-specific user interface.

FIG. 3A is a plan view of a first embodiment of a bedside interface device comprising a computer 26a, suitable for use in the EP lab of FIG. 2, and showing a first application-specific user interface. The computer 26a includes a touch-responsive display panel and thus may be referred to hereinafter sometimes as a touch panel computer. The touch panel computer 26a, as shown in inset in FIG. 3A, includes an electronic control unit (ECU) having a processor 60 and a computer-readable memory 62, user interface (UI) logic 64 stored in the memory 62 and configured to be executed by processor 60, a microphone 66 and voice recognition logic 68. In an embodiment, voice recognition logic 68 is also stored in memory 62 and is configured to be executed by processor 60. In an embodiment, the touch panel computer 26a is configured for wireless communication to base interface 28 (best shown in FIG. 2). In addition, the touch panel computer 26a is configured to draw operating power at least from a battery-based power source—eliminating the need for a power cable. The resulting portability (i.e., no cables needed for either communications or power) allows touch panel computer 26a to be carried around by the EP physician 16 or other lab staff to provide control over the linked systems (described below) while moving throughout the procedure room 10 or even the control room 12. In another embodiment, touch panel computer 26a can be wired for one or both of communications and power, and can also be fixed to the bedrail or in the sterile field.

In the illustrated embodiment, the UI logic 64 is configured to present a plurality of application-specific user interfaces, each configured to allow a user (e.g., the EP physician 16) to interact with a respective one of a plurality of diagnostic and/or therapeutic systems (and their unique interface or control applications). As shown in FIG. 3A, the UI logic 64 is configured to present on the touch panel surface of computer 26a a plurality of touch-sensitive objects (i.e., "buttons", "flattened joystick", etc), to be described below. In the illustrative embodiment, the UI logic 64 produces a first, application-selection group of buttons, designated as group 70, and which are located near the top of the touch panel. Each of the buttons in group 70 are associated with a respective diagnostic and/or therapeutic system (and control or interface application therefore). For example, the six buttons labeled "EnSite", "WorkMate", "EP4", "NurseMate", "MediGuide", "ViewMate" correspond to electro-anatomic mapping system 34 (for mapping control), EP recording system 38 (for patient data recording control), stimulator 40 (for stimulator control), EP data editing and monitoring system 42 (for charting) and ultrasound imaging system 32 (for ultrasound control), respectively.

When a user selects one of the buttons in group 70, the UI logic 64 configures the screen display of computer 26a with an application-specific user interface tailored for the control of and interface with the particular EP system selected by the user. In FIG. 3A, the "EnSite" system is selected, so the UI logic 64 alters the visual appearance of the "EnSite" button so that it is visually distinguishable from the other, non-selected buttons in group 70. For example, when selected, the "EnSite" button may appear depressed or otherwise shaded differently than the other, non-selected buttons in group 70. This always lets the user know what system is selected. The UI logic 64, in an embodiment, also maintains the application-selection buttons in group 70 at the top of the screen regardless of the particular application selected by the user. This arrangement allows the user to move from system (application) to system (application) quickly and control each one independently.

With continued reference to FIG. 3A, UI logic 64 presents an application-specific user interface tailored and optimized for control of and interaction with system 34. This user interface includes a second, common-task group of selectable buttons, designated group 72, a third, view-mode group of selectable buttons, designated group 74, a fourth, view-select group of selectable buttons, designated group 76, a flattened joystick 78 configured to receive view-manipulation input from the user, a voice recognition control button 80, and a settings button 82. Each group will be addressed in turn.

The second group 72 of buttons includes a listing of common tasks performed by an EP physician when interacting with system 34. Each of the buttons in group 72 are associated with a respective task (and resulting action). For example, the five buttons in group 72 are labeled "Zoom In", "Zoom Out", "Add Lesion", "Freeze Point", and "Save Point". The "Zoom In" and "Zoom Out" buttons allow the user to adjust the apparent size of the 3D model displayed on monitor 20 (i.e., enlarging or reducing the 3D model on the monitor).

Figure 4A:
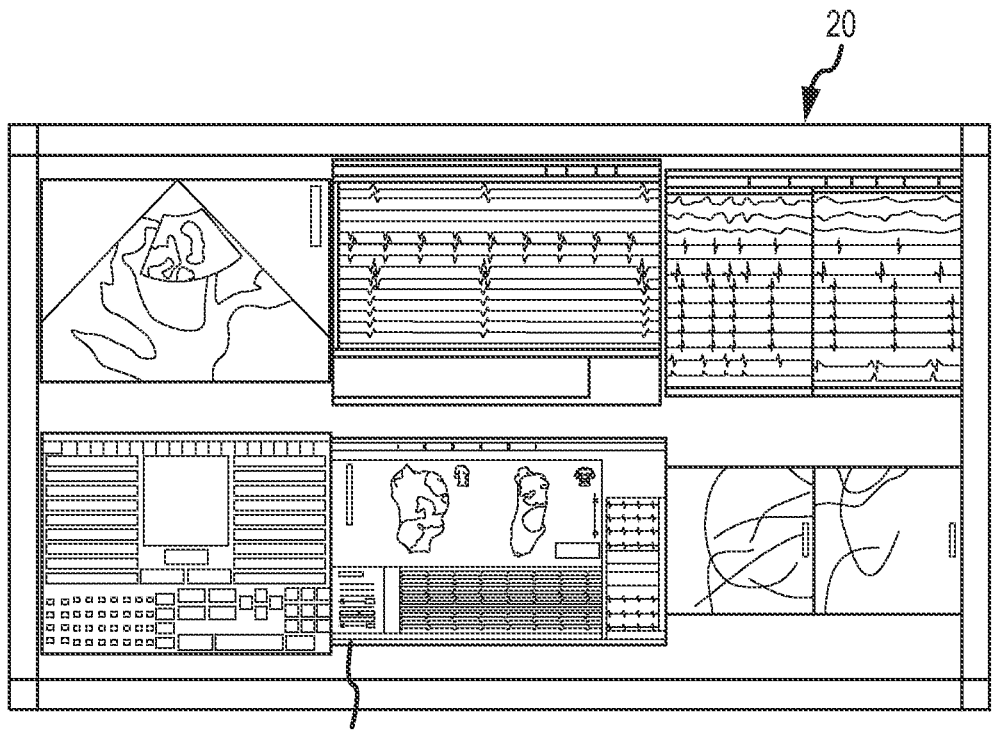
FIG. 4A is a view of a monitor shown in FIG. 2, showing multiple inset displays associated with a plurality of diagnostic and/or therapeutic systems.
Figure 4B:
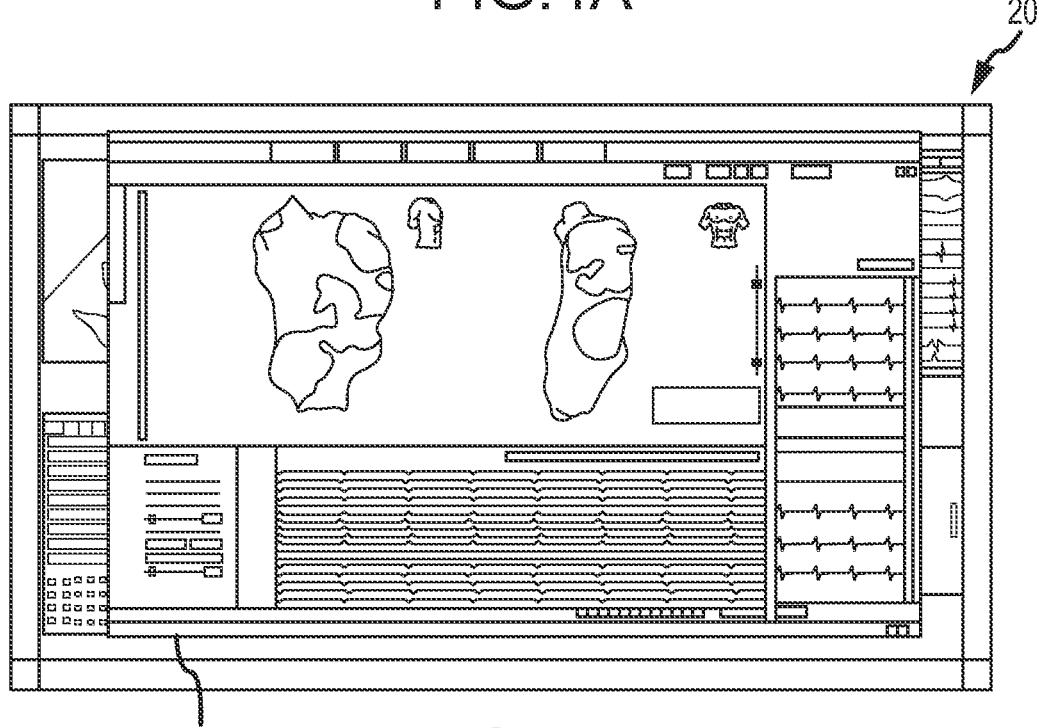
FIG. 4B is a view of the monitor of FIG. 4A, showing a zoomed-in window of the display associated with an electro-anatomic mapping system.

For example, FIG. 4A is a view of the monitor 20 of FIG. 2, showing multiple inset displays for different applications, where the display area (window) 52₁ shows the EnSite™ display output of a 3D electro-anatomic model at a first magnification level. FIG. 4B is a further view of monitor 20, showing a zoomed-in view of the same display area (window), now designated 52₂, which has an increased magnification level and thus apparent size. This change of course allows the physician to see details in window 52₂ that may not be easy to see in window 52₁.

Referring again to FIG. 3A, the "Add Lesion" button is configured to add a lesion marker to the 3D model. Other commands can be also be executed using the "Freeze Point" and "Save Point" buttons. It should be understood that variations are possible.

Each of the buttons in group 74 are associated with a respective display mode, which alters the display output of system 34 to suit the wishes of the physician. For example, the three selectable buttons labeled "Dual View", "Right View", and "Map View" re-configure the display output of system 34, as will appear on monitor 20.

Each of the buttons in group 76 are associated with a respective viewpoint from which the 3D electro-anatomic model is "viewed" (i.e., as shown in window 52 on monitor 20). Three of the five selectable buttons, namely those labeled "LAO", "AP", and "RAO", allow the user to reconfigure the view point from which the 3D electro-anatomic model is viewed (i.e., left anterior oblique, anterior-posterior, right anterior oblique, respectively). The remaining two buttons, namely those labeled "Center at Surface" and "Center at Electrode" allow the user to invoke, respectively, the following functions: (1) center the anatomy shape in the middle of the viewing area; and (2) center the current mapping electrode or electrodes in the middle of the viewing area.

The flattened joystick 78 is a screen object that allows the user to rotate the 3D model displayed in the window 52. In addition, as the point of contact (i.e., physician's finger) with the joystick object 78 moves from the center or neutral position, for example at point 83, towards the outer perimeter (e.g., through point 84 to point 86), the magnitude of the input action increases. For example, the acceleration of rotation of the model or cursor will increase. While FIG. 3A shows the joystick object 78 as having three (3) gradations or concentric bands, it should be appreciated that this is for clarity only and not limiting in number. For example, in an embodiment, a relatively larger number of gradations or bands, such as ten (10), may be provided so as to effectively provide for a substantially continuous increase in sensitivity (or magnitude) as the point of contact moves toward the outer radius. In another embodiment, a single gradient may be continuous from the center position, point 83, to the outer edge of the joystick object 78, with the centermost portion of the gradient being the brightest in intensity or color and the outermost portion of the gradient being the darkest in intensity or color, for example. In yet another embodiment, a single gradient may be continuous from the center position, point 83, to the outer edge of the joystick object 78, with the centermost portion of the gradient being the darkest in intensity or color and the outermost portion of the gradient being brightest in intensity or color, for example.

In a further embodiment, UI logic 64 can be further configured to present an additional button labeled "Follow Me" (not shown), which, when selected by the user, configures the electro-anatomic mapping system 34 for "follow me" control. This style of control is not currently available using a conventional keyboard and mouse interface. For "follow me" control, UI logic 64 is configured to receive a rotation input from the user via the touch panel (e.g., joystick 78); however, the received input is interpreted by system 34 as a request to rotate the endocardial surface rendering (the "map") while maintaining the mapping catheter still or stationary on the display. In an embodiment, the physician can set the position and orientation of the mapping catheter, where it will remain stationary after the "Follow Me" button is selected.

Another feature of the touch panel computer 26a is that it incorporates, in an embodiment, voice recognition technology. As described above, computer 26a includes microphone 66 for capturing speech (audio) and voice recognition logic 68 for analyzing the captured speech to extract or identify spoken commands. The voice recognition feature can be used in combination with the touch panel functionality of computer 26a. The microphone 66 may comprise conventional apparatus known in the art, and can be a voice recognition optimized microphone particularly adapted for use in speech recognition applications (e.g., an echo-cancelling microphone). Voice recognition logic 68 may comprise conventional apparatus known in the art. In an embodiment, voice recognition logic 68 may be a commercially available component, such as software available under the trade designation DRAGON DICTATION™ speech recognition software.

In an embodiment, computer 26a is configured to recognize a defined set of words or phrases adapted to control various functions of the multiple applications that are accessible or controllable by computer 26a. The voice recognition feature can itself be configured to recognize unique words or phrases to selectively enable or disable the voice recognition feature. Alternatively (or in addition to), a button, such as button 80 in FIG. 3A, can be used to enable or disable the voice recognition feature. In this regard, the enable/disable button can be either a touch-sensitive button (i.e., screen object), or can be hardware button.

Voice recognition logic 68 is configured to interact with the physician or other user to "train" the logic (e.g., having the user speak known words) so as to improve word and/or phrase recognition. The particulars for each user so trained can be stored in a respective voice (user) profile, stored in memory 62. For example, in FIG. 3A, the currently active voice profile is listed in dashed-line box 89. In an embodiment, each user can have unique commands, which may also be stored in the respective voice profile. In a further embodiment, the language need not be English, and can be other languages. This flexibility as to language choice enlarges the audience of users who can use the device 26a. The voice recognition feature presents a number of advantages, including the fact that the physician 16 does not have to remove his/her hands from the catheter or other medical device being manipulated. In addition, the absence of contact or need to touch computer 26a maintains a sterile condition. The voice recognition feature can also be used either alone or in combination with other technologies.

With continued reference to FIG. 3A, UI logic 64 also presents a "Settings" button 82. When the "Settings" button 82 is selected, UI logic 64 generates another screen display that allows the user to adjust and/or set/reset various settings associated with the application currently selected. In an embodiment, the "Settings" button can also allow adjustment of parameters that are more global in nature (i.e., apply to more than one application). For example only, through "Settings", the physician or another user can edit all of the phrases associated with a particular physician or specify a timeout (i.e., the elapsed amount of time, after which the computer will stop listening (or not) for voice commands). The physician or another user can also edit miscellaneous parameters, such as communication settings and the like.

Figure 3B:
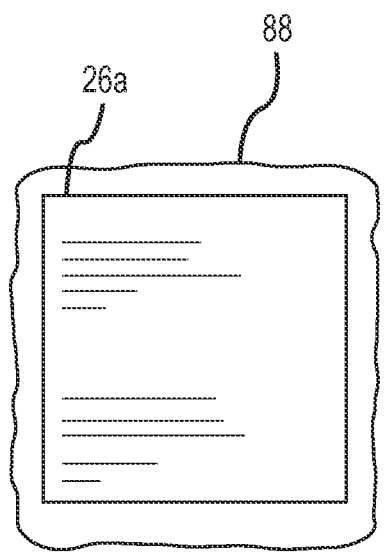
FIG. 3B is an isometric view of a sterile drape configured to isolate the touch panel computer of FIG. 3A.

FIG. 3B is an isometric view of a sterile drape 88 configured to protect the touch panel computer 26a of FIG. 3A from contamination and to maintain the physician's sterility. Conventional materials and construction techniques can be used to make drape 88.

Figure 5:
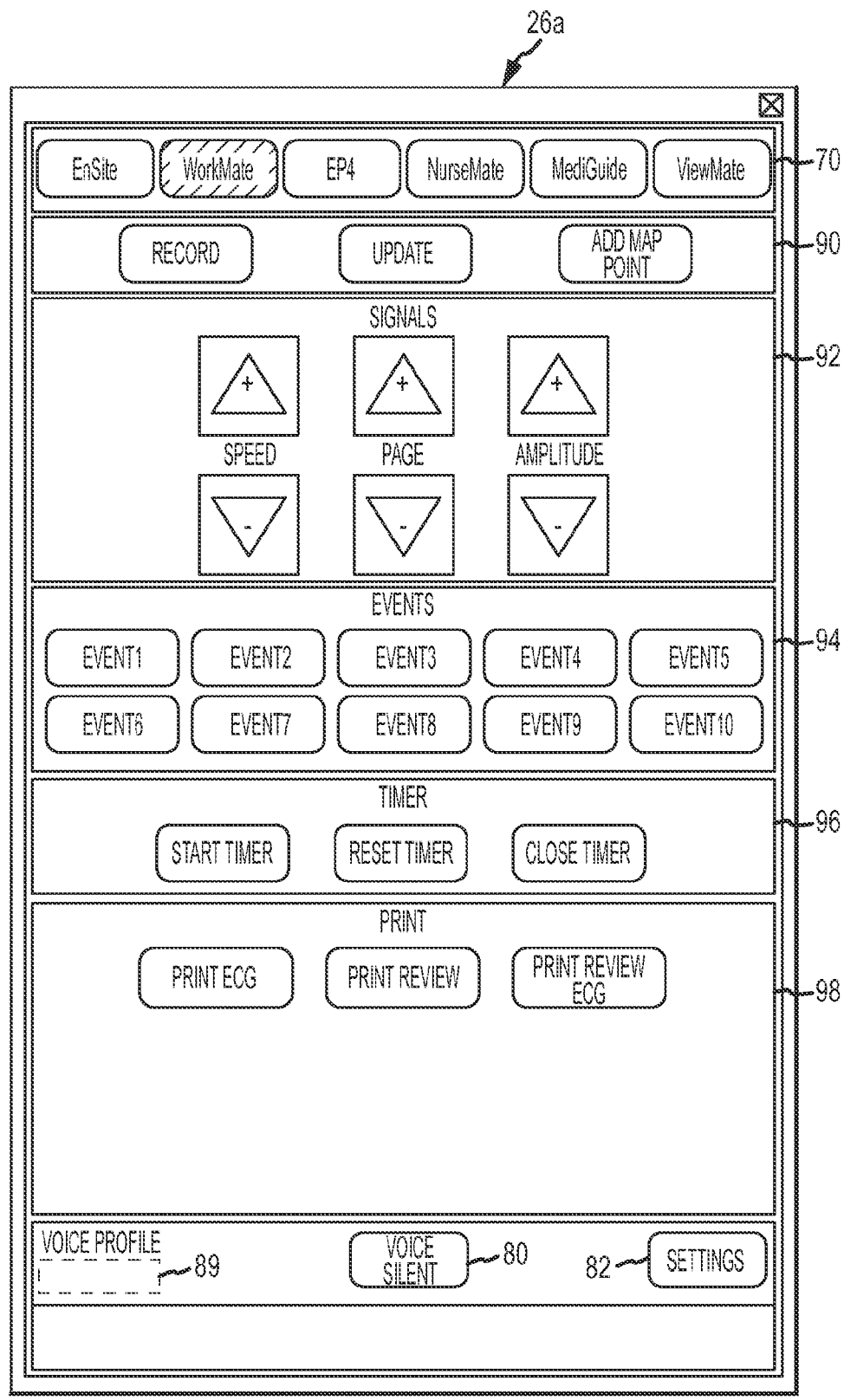
FIG. 5 is a plan view of the touch panel computer of FIG. 3A showing a second application-specific user interface.

FIG. 5 is a plan view of touch panel computer 26a showing a different application-specific user interface, now relating to EP monitoring and recording system 38 (i.e., "EP-Work-Mate"). In the illustrative embodiment, UI logic 64 produces the same application-selection group 70 of buttons along the top of the touch panel, for quick and easy movement by the user between applications. A second, common-tasks group of buttons, designated as group 90, are shown below group 70. For example, the three buttons labeled "Record", "Update", and "Add Map Point" can execute the identified function Likewise, additional groups of buttons are shown, grouped by function, for example the signals-adjustment group 92, the events group 94, the timer group 96 and the print group 98. It should be understood that variations are possible, depending on the items that can be adjusted or controlled on the destination system. It warrants emphasizing that UI logic 64 thus presents a unique user interface tailored to the requirements of the particular application selected. Each group includes items that are commonly asked for by the physician. For example, in the signals group 92, the Speed +/− buttons can be used to change the viewed waveform sweep speed as the physician may need more or less detail; the Page +/− buttons can be used to change the page of signals being viewed (e.g., from surface ECG signals to intracardiac signals); and the Amplitude +/− buttons can be used to change the signal amplitudes up or down. As a further example, in the Events group 94, the enumerated Events buttons cause a mark to be created in the patient charting log to indicate a noteworthy (i.e., important) item or event, such as the patient was just defibrillated or entered a tachy-arrhythmia. Note that these items are all user definable and speakable (capable of being tied to the voice recognition function). The physician also needs to keep track of certain periods of time. Thus, in the Timer group 96, the timer buttons can be used to keep track of such periods of time, for example, such as a certain time after an ablation (e.g., 30 minutes) to verify that the ablation procedure is still effective. Finally, regarding the print group 98, various print buttons are provided so as to avoid requiring a physician to verbally indicate (e.g., by way of shouting out "print that document to the case" or the like) and to include such documents in a final report.

Figure 6:
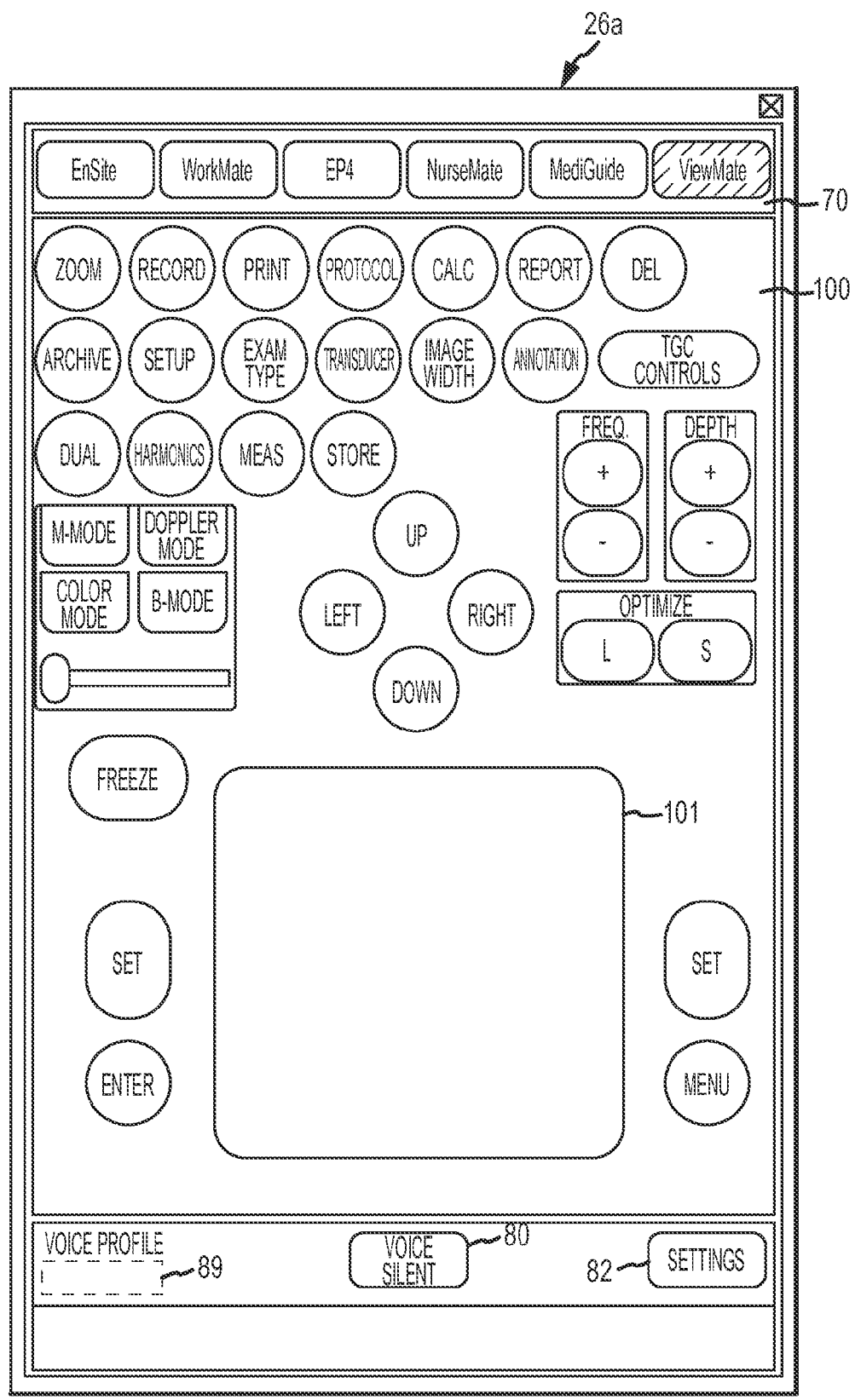
FIG. 6 is a plan view of the touch panel computer of FIG. 3A showing a third application-specific user interface.

FIG. 6 is a plan view of touch panel computer 26a showing in exemplary fashion a further, different application-specific user interface relating to the ultrasound imaging system 32 ("ViewMate"). As with the other application-specific user interfaces, the user interface presented in FIG. 6 repeats the common, application-selection group of buttons, designated group 70. A further group of buttons and adjustment mechanisms are located in group 100. The controls (buttons, sliders) provided for this user interface completely eliminate the need to have a separate ultrasound keyboard to control the console. The user interface shown can be different, independent on the kind of machine being controlled, but at a minimum may typically provide a way to control the receive gain, the depth setting, the focus zone, the TGC (i.e., time gain compensation) curve, the monitoring mode (e.g., B, M, color Doppler, Doppler), image recording, as well as other image attributes and states. Note, trackpad object 101 is shown in the center of the user interface. The capability provided by UI logic 64 to rapidly switch applications and present to the bedside user an application-specific user interface minimizes or eliminates many of the shortcomings set forth in the Background.

It should be understood that variations in UI logic 64 are possible. For example, certain applications can be linked (in software) so that multiple applications can be controlled with a single command (e.g., the Record command). In another embodiment, UI logic 64 can be configured to provide additional and/or substitute functions, such as, without limitation, (1) map creation; (2) collecting points; (3) segmenting regions by anatomy; (4) map view (rotate and zoom); (5) select/manipulate a number of maps and view each; (6) selection of signal trace display; (7) adjust EP signal amplitude; (8) sweep speed; (9) provide single button (or touch, multi-touch, gesture) for recording a segment, placing an event marker, and/or placing a lesion marker.

It should be further understood that the screen layouts in the illustrative embodiment are exemplary only and not limiting in nature. The UI logic 64 can thus implement alternative screen layouts for interaction by the user. For example, while the screen displays in FIGS. 3A, 5 and 6 show an approach that incorporates the top level menu items on every screen, multi-level menus can also be used. For example, the screen layouts can be arranged such that a user descends down a series of screens to further levels of control. To return to upper levels (and to the "home" screen), a "Back" button or the like can be provided. Alternatively, a "Home" button can be provided.

In a still further embodiment, UI logic 64 can be configured for bi-directional display of information, for example, on the touch-responsive display panel. As one example, the "EnSite" user interface (FIG. 3A) can be configured so that the EnSite™ model is sent to the computer 26a and displayed on the touch-responsive display panel. The user interface provided by UI logic 64 can allow the user to drag his or her finger on the panel to rotate the model. The display of the model provides context with respect to the act of dragging. Other information can be displayed as well, such as a waveform. In various embodiments, all or a portion of the items/windows displayed on monitor 20 (see, e.g., FIGS. 2, 4A, and 4B) may be displayed or mirrored on the touch-responsive display panel. For example, display area or window 52 may be displayed on the touch-responsive display panel allowing the physician or other user to directly modify the features of window 52 at the patient's bedside. Other display areas/windows, such as windows 50, 54, 56, 58, and/or 48 (see FIG. 2) may also be displayed and/or modified on the touch-panel display panel. One further example involves displaying feedback information or messages originating from the various devices or systems back to the touch-responsive display panel. In this regard, the UI logic 64 can configure any of the user-interfaces to have a message area, which can show informational messages, warning messages or critical error messages for viewing by the user. The message area feature provides a way to immediately alert the physician to such messages, rather than the physician having to watch for messages on multiple displays.

Figure 7A:
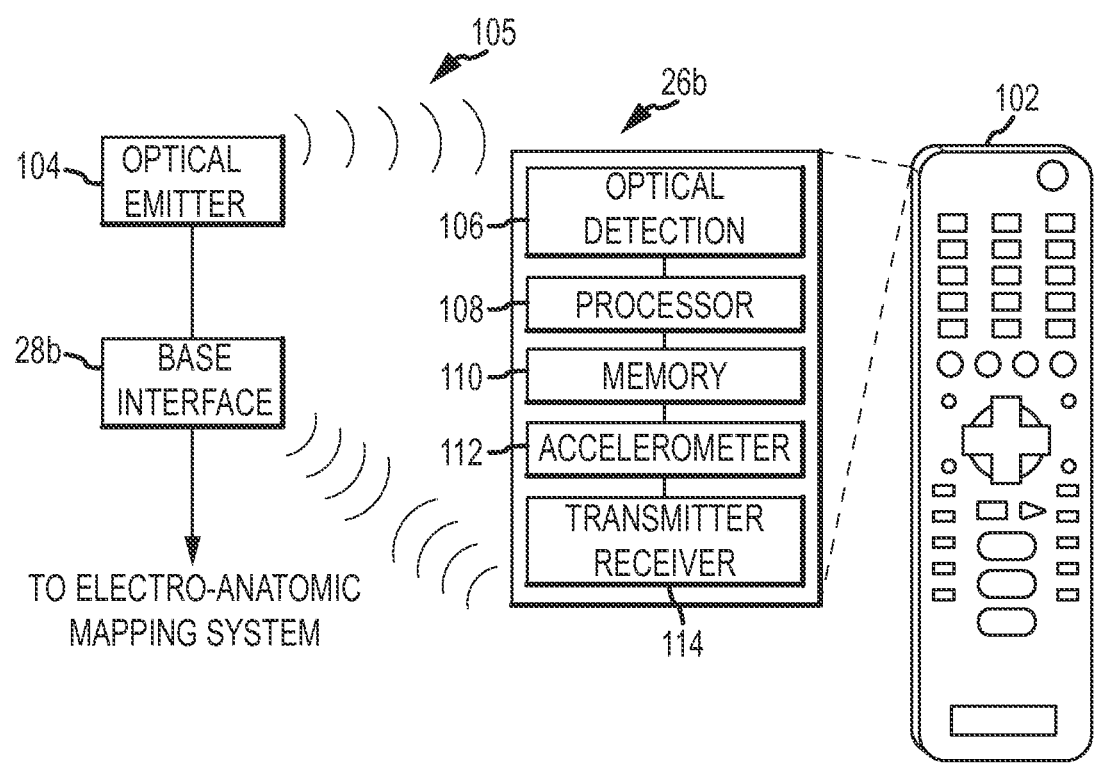
FIG. 7A is a diagrammatic and block diagram view of a second embodiment of the bedside interface device comprising an electronic wand system.

FIG. 7A is a diagrammatic and block diagram view of a second embodiment of the bedside interface device, comprising an electronic wand system 26b. As with touch panel computer 26a, wand system 26b is configured to allow the EP physician to take control, bedside of the patient, of an EP diagnostic or therapeutic system, such as the electro-anatomic mapping system 34. The wand system 26b includes a wireless remote control portion 102, an optical emitter portion 104, and a base interface 28b, which may be coupled to the desired, target EP system through either a wired or wireless connection. The wand system 26b incorporates remote control technology, and includes the ability to detect and interpret motion of the remote control indicative of an EP physician's command or other instruction, detect and interpret key-presses on the remote control, and/or detect and interpret motion/keypress combinations.

Since the wand system 26b is contemplated as being used in the sterile procedure room, multiple embodiments are contemplated for avoiding contamination. In this regard, wand system 26b may be configured with a disposable remote control portion 102, with a reusable remote control portion 102 that is contained within an enclosure compatible with sterilization procedures, with a reusable remote control portion 102 adapted to be secured in a sterilization-compatible wrapper, or with a reusable remote control portion 102 that is encased in a sterile but disposable wrapper.

With continued reference to FIG. 7A, remote control portion 102 may include an optical detector 106, an electronic processor 108, a memory 110, an optional accelerometer 112 and a wireless transmitter/receiver 114. The processor 108 is configured to execute a control program that is stored in memory 110, to achieve the functions described below. The optical emitter 104 is configured to emit a light pattern 105 that can be detected and recognized by optical detector 106. For example, the light pattern may be a pair of light sources spaced apart by a predetermined, known distance. The control program in remote 102 can be configured to assess movement of the light pattern 105 as detected by detector 106 (e.g., by assessing a time-based sequence of images captured by detector 106). For example, in the exemplary light pattern described above, processor 108 can be configured to determine the locations of the light sources (in pixel space). In an embodiment, the control program in remote 102 may only discern the light pattern 105 itself (e.g., the locations in pixel space) and transmit this information to base interface 28b, which in turn assesses the movement of the detected light pattern in order to arrive at a description of the motion of the remote 102. In a still further embodiment, various aspects of the processing may be divided between processor 108 and a processor (not shown) contained in base interface 28b. The processor 106 communicates with base interface 28b via the wireless transmitter/receiver 114, which may be any type of wireless communication method now known or hereafter developed (e.g., such as those technologies or standards branded Bluetooth™, Wi-Fi™, etc.). The processor 108 is configured to transmit wirelessly to interface 28b the detected keypresses and information concerning the motion of the remote control 102 (e.g., the information about or derived from the images from the optical detector 106). In an embodiment, the motion of remote control 102 may also be determined, or supplemented by, readings from accelerometer 112 (which may be single-axis or multi-axis, such as a 3-axis accelerometer). In some instances, rapid motion may be better detected using an accelerometer than using optical methods. In an embodiment, electronic wand system 26b may be similar to (but differing in application, as described herein) a commercially available game controller sold under the trade designation Wii Remote Controller, from Nintendo of America, Inc.

Either the remote 102 or the base interface 28b (or both, potentially in some division of computing labor) is configured to identify a command applicable to the one of the EP diagnostic/therapeutic systems, such as electro-anatomic mapping system 34, based on the detected motion of the remote 102. Alternatively, the command may be identified based on a key press, or a predetermined motion/key press combination. Once the remote 102 and/or interface 28b identifies the command it is transmitted to the appropriate EP system. In an electro-anatomic mapping system embodiment, the wireless remote control 102 is configured to allow an EP physician to issues a wide variety of commands, for example only, any of the commands (e.g., 3D model rotation, manipulation, etc.) described above in connection with touch panel computer 26a. By encoding at least some of the control through the wireless remote control 102 that the EP physician controls, one or more of the shortcomings of conventional EP labs, as described in the Background, can be minimized or eliminated. As with touch panel computer 26a, electronic wand system 26b can reduce procedure times as the EP physician will spend less time playing "hot or cold" with the mapping system operator (i.e., the control technician), but instead can set the display to his/her needs throughout the medical procedure.

Figure 7B:
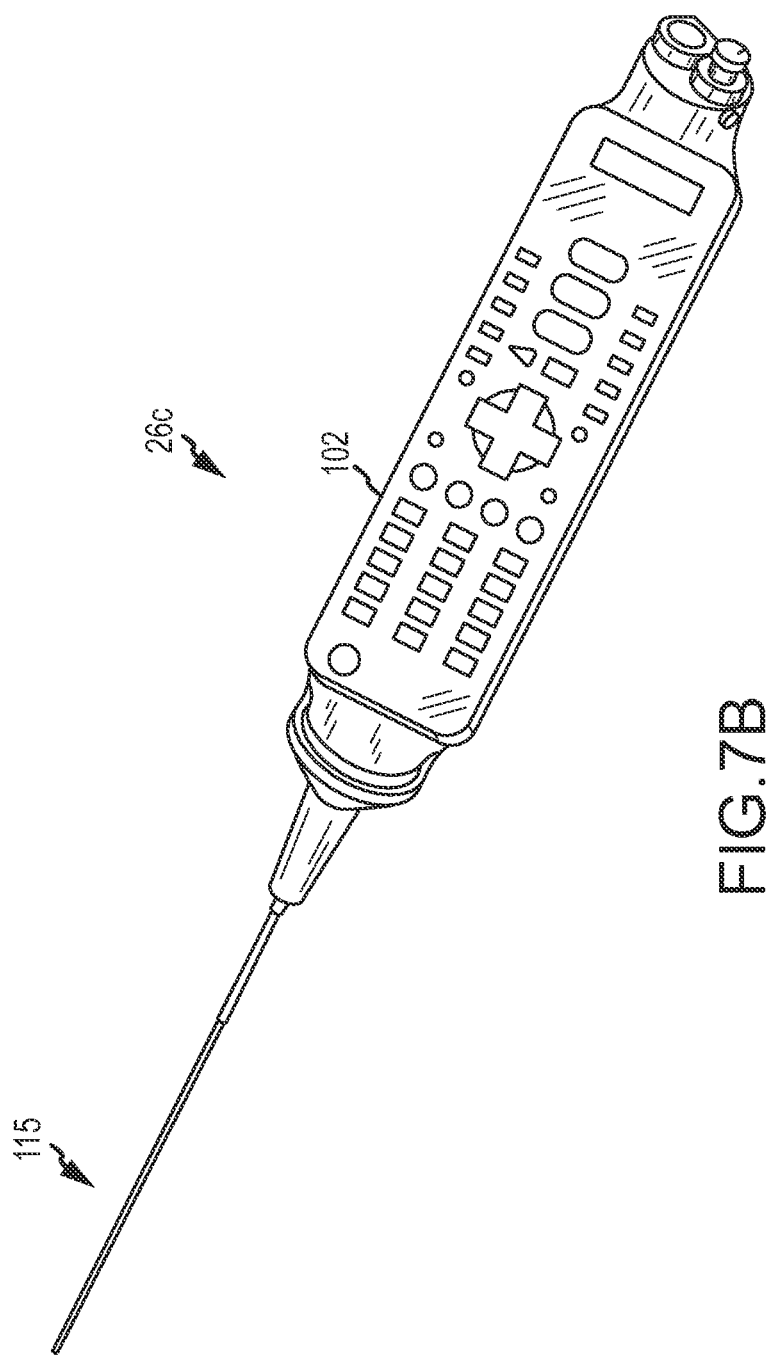
FIG. 7B is a diagrammatic view of a third embodiment of the bedside interface device wherein a catheter is integrated with the remote control portion of FIG. 7A.

FIG. 7B shows a further embodiment, designated interface device 26c. Interface device 26 integrates the remote control 102 described above into the handle of a catheter 115. Through the foregoing, the physician need not take his hands off the catheter, but rather can issue direct, physical commands (e.g., via key-presses) while retaining control of the catheter. Additionally, one or more of the keys or a slider switch on the catheter handle may serve as a safety mechanism to prevent inadvertent activation of one or more commands while operating the catheter. In such an embodiment, after advancing the catheter into a patient's body, the safety mechanism may be deactivated or otherwise turned off such that the physician can issue commands and then he or she may reactivate or turn on the safety mechanism and resume manipulating the catheter without fear of modifying the view or model shown on an on-screen display, for example. The catheter 115 may further comprise one or more electrodes on a distal portion of the catheter shaft and a manual or motorized steering mechanism (not shown) to enable the distal portion of the catheter shaft to be steered in at least one direction. In at least one embodiment, the catheter handle may be generally symmetric on opposing sides and include identical or nearly identical sets of controls on opposing sides of the handle so that a physician need not worry about which side of the catheter handle contains the keys. In another embodiment, the catheter handle may be generally cylindrical in shape and include an annular and/or rotatable control feature for issuing at least one command, again so the physician need not worry about the catheter handle's orientation in his or her hand(s). Exemplary catheters, handles, and steering mechanisms are shown and described in U.S. Pat. No. 5,861,024 to Rashidi, U.S. patent application publication no. 2010/0314031 to Heideman et al., U.S. Pat. No. 7,465,288 to Dudney et al., and U.S. Pat. No. 6,671,533 to Chen et al., each of which is hereby incorporated by reference as though fully set forth herein.

Figure 8:
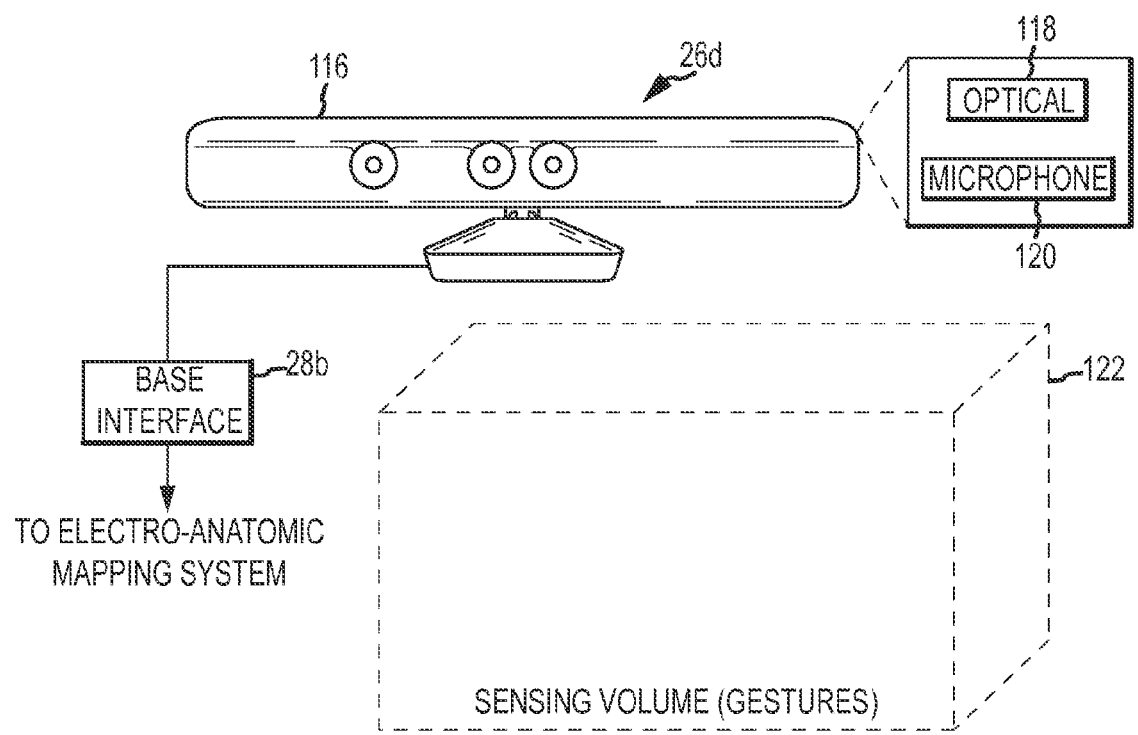
FIG. 8 is a diagrammatic and block diagram view of a fourth embodiment of the bedside interface device comprising a motion capture apparatus.

FIG. 8 is a diagrammatic and block diagram view of a fourth embodiment of the bedside interface device, comprising a motion capture apparatus 26d. As with touch panel computer 26a, wand system 26b and integrated system 26c, motion capture apparatus 26d is configured to allow the EP physician to take control, bedside of the patient, of an EP diagnostic or therapeutic system, such as electro-anatomical mapping system 34. The motion capture apparatus 26d includes a capture apparatus 116 having both an optical sub-system 118 and a microphone sub-system 120 where the apparatus 116 is coupled to a base interface 28b. The apparatus 116 is configured to optically detect the motion or physical gestures of the EP physician or other user when such movements occur within a sensing volume 122. The base interface 28b may be coupled to the desired, target EP system through either a wired or wireless connection.

The motion capture apparatus 26d includes the capability to detect hand/arm/leg/trunk/facial motions (e.g., gestures) of the EP physician or other user and translate the detected patterns into a desired command. Apparatus 26d also includes audio capture and processing capability and thus also has the capability to detect speech and translate the same into desired commands. In an embodiment, apparatus 26d is configured to detect and interpret combinations and sequences of gestures and speech into desired commands. The base interface 28b is configured to communicate the commands (e.g., rotation, zoom, pan of a 3D anatomical model) to the appropriate EP diagnostic or therapeutic system (e.g., the electro-anatomic mapping system 34). In an embodiment, the motion capture apparatus 26d may comprise commercially available components, for example, the Kinect™ game control system, available from Microsoft, Redmond, Wash., USA. A so-called Kinect™ software development kit (SDK) is available, which includes drivers, rich application programming interfaces (API's), among other things contents, that enables access to the capabilities of the Kinect™ device. In particular, the SDK allows access to raw sensor streams (e.g., depth sensor, color camera sensor, and four-element microphone array), skeletal tracking, advanced audio (i.e., integration with Windows speech recognition) as well as other features.

Since there is no contact contemplated by EP physician 16 during use of motion capture apparatus 26d, contamination and subsequent sterilization issues are eliminated or reduced. In addition, the lack of contact with apparatus 26d for control purposes allows the EP physician to keep his hands on the catheter or other medical device(s) being manipulated during an EP procedure. By encoding at least some of the control through the motion capture apparatus 26d, with which the EP physician interacts, one or more of the shortcomings of conventional EP labs, as described in the Background, can be minimized or eliminated. As with the previous embodiments, the motion capture apparatus 26d can reduce procedure times.

It should be understood that variations are possible. For example, the motion capture apparatus 26d can be used in concert with sensors and/or emitters in a sterile glove to assist the apparatus 26d to discriminate commands intended to be directed to one of the EP systems, versus EP physician hand movements that result from his/her manipulation of the catheter or medical device, versus other movement in the EP lab in general. In another embodiment, the motion capture apparatus 26d may discriminate such commands by being "activated" by a user when a specific verbal command is issued (e.g., "motion capture on") and then "deactivated" by the user when another specific verbal command is issued (e.g., "motion capture off").

Figure 9:
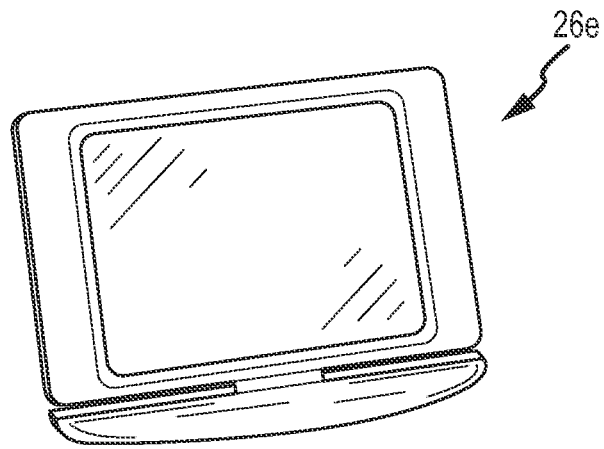
FIGS. 9-10 are diagrammatic views of fifth and sixth embodiments of the bedside interface device comprising touch responsive surface devices that can be covered in a sterile bag.
Figure 10:
Figure 10:
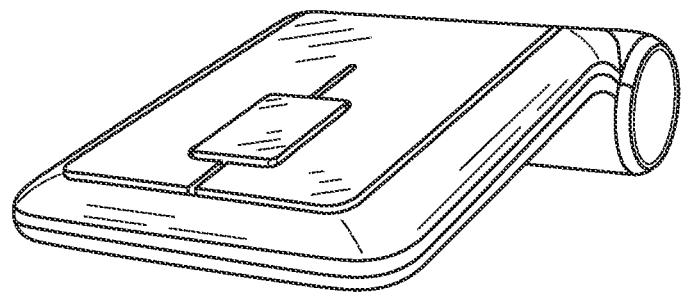

FIGS. 9-10 are diagrammatic views of fifth and sixth embodiments of the bedside interface device, comprising touch responsive devices. FIGS. 9 and 10 show touch-screen mouse pad devices 26e and 26f, respectively. These devices can be covered in a sterile bag. The EP physician 16 can move the mouse cursor from application to application and control each such application independently. Devices 26e, 26f may comprise conventional apparatus known in the art.

Figure 11:
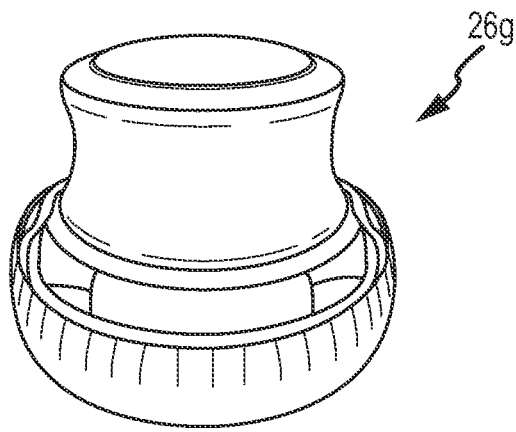
FIG. 11 is a diagrammatic view of a seventh embodiment of the bedside interface device comprising a customized joystick that can be covered in a sterile bag.

FIG. 11 is a diagrammatic view of a seventh embodiment of the bedside interface device comprising a customized joystick 26g. Joystick 26g can also be covered in a sterile bag. The device 26g can be used to be provide application-specific control a particular application function(s), such as rotating a 3D model (system 34), adding lesion markers, and the like.

Figure 12:
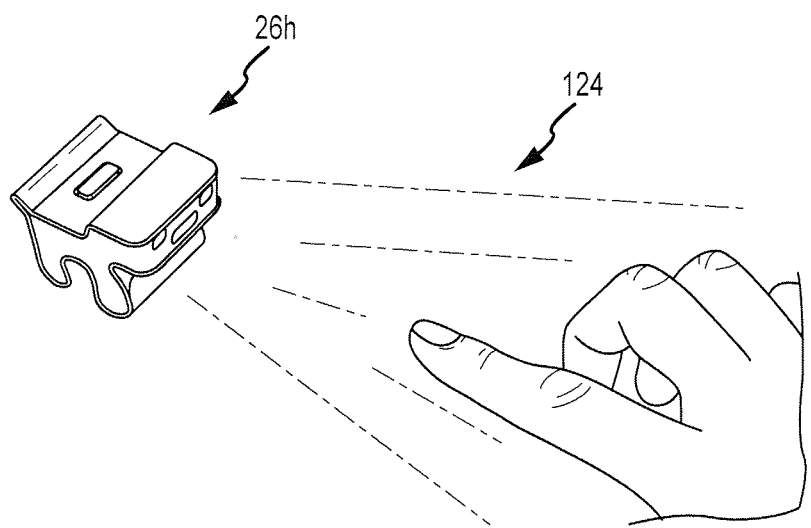
FIGS. 12-13 are diagrammatic views of eighth and ninth embodiments of the bedside interface device comprising holographic mouse and keyboard input devices, respectively.
Figure 13:
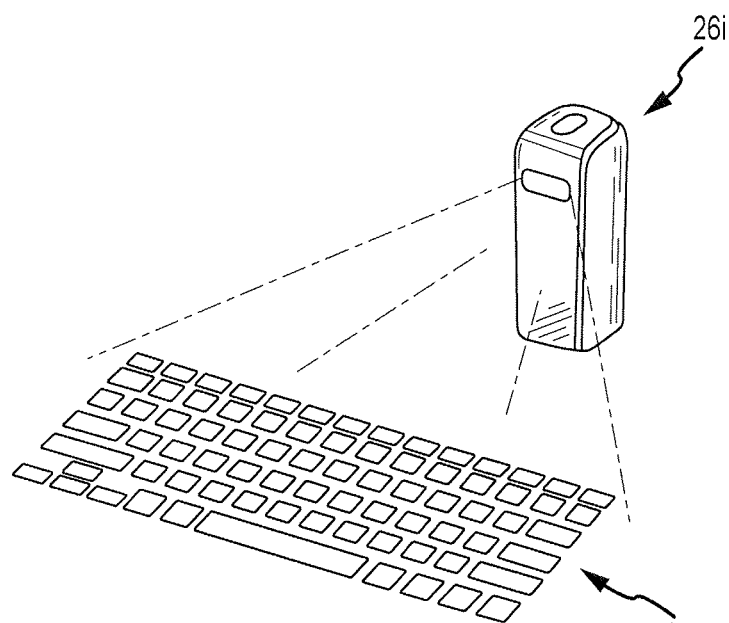

FIGS. 12-13 are diagrammatic views of eighth and ninth embodiments of the bedside interface device comprising holographic mouse and keyboard input devices, respectively. Holographic mouse 26h deploys light beam pattern 124, which is used by the mouse 26h to acquire user input (i.e., movement of the physician's finger, instead of moving a conventional mouse). The movement input can be used in the same manner as that obtained from a conventional mouse. Holographic keyboard 26i also deploys a light beam pattern 126 corresponding to a keyboard. A physician's finger can be used to "select" the key much in the same manner as a conventional keyboard, but without any physical contact. Devices 26h, 26i have the advantage of being sterile without any disposables, and can incorporate wireless communications and may be powered using batteries (i.e., no cables needed).

It should be understood that variations are possible. For example, in a further embodiment, primary control by the physician in manipulating or interacting with the mapping system may be through use of voice control alone (i.e., a microphone coupled with voice recognition logic), apart from its inclusion with other modes or devices for user interaction described above. In a still further embodiment, the physician can be equipped with headgear that monitors head movements to determine at what location on the screen/monitor the physician is looking. In effect, such headgear can act as a trackball to move or otherwise manipulate an image (or view of a model) on the monitor in accordance with the physician's head movements. In a yet further embodiment, the physician can be equipped with headgear that monitors head movements and/or also monitors brainwave patterns (e.g., to record a user electroencephalogram (EEG)). Such monitored data can be analyzed to derive or infer user input or commands for controlling an image (or view of a model), as described above. An EEG-based embodiment may comprise conventional apparatus known in the art, for example, commercially available products respectively sold under the trade designation MindWave™ headset from NeuroSky, Inc., San Jose, Calif., USA, or the Emotiv EPOC™ personal interface neuroheadset from Emotiv, Kwun Tong, Hong Kong. In a still further embodiment, the physician can be equipped with an eye tracking apparatus, wherein monitored eye movements constitute the user input to be interpreted by the system (e.g., the eye movements can be interpreted as a cursor movement or other command).

It should also be appreciated that while the foregoing description pertains to an EP physician manually controlling a catheter through the use of a manually-actuated handle or the like, other configurations are possible, such as robotically-actuated embodiments. For example, a catheter movement controller (not shown) described above may be incorporated into a larger robotic catheter guidance and control system, for example, as seen by reference to U.S. application Ser. No. 12/751,843 filed Mar. 31, 2010 entitled ROBOTIC CATHETER SYSTEM (published as U.S. patent application publication no. 2010/0256558), owned by the common assignee of the present invention and hereby incorporated by reference in its entirety as though fully set forth herein. Such a robotic catheter system may be configured to manipulate and maneuver catheters within a lumen or a cavity of a human body, while the bedside interface devices described herein can be used to access and control the EP diagnostic and/or therapeutic systems. In at least one embodiment, a bedside interface device as described herein may also be used to access and control the robotic catheter system.

In accordance with another embodiment, an article of manufacture includes a computer storage medium having a computer program encoded thereon, where the computer program includes code for acquiring user input based on at least one of a plurality of input modes, such as by touch, multi-touch, gesture, motion pattern, voice recognition and the like, and identifying one or more commands or requests for an EP diagnostic and/or therapeutic system. Such embodiments may be configured to execute one or more processors, multiple processors that are integrated into a single system or are distributed over and connected together through a communications network, and where the network may be wired or wireless.

It should be understood that while the foregoing description describes various embodiments of a bedside interface device in the context of the practice of electrophysiology, and specifically catheterization, the teachings are not so limited and can be applied to other clinical settings.

It should be understood that the an electronic control unit as described above may include conventional processing apparatus known in the art, capable of executing pre-programmed instructions stored in an associated memory, all performing in accordance with the functionality described herein. It is contemplated that the methods described herein may be programmed, with the resulting software being stored in an associated memory and where so described, may also constitute the means for performing such methods. Implementation of an embodiment of the invention, in software, in view of the foregoing enabling description, would require no more than routine application of programming skills by one of ordinary skill in the art. Such a system may further be of the type having both ROM, RAM, a combination of non-volatile and volatile (modifiable) memory so that the software can be stored and yet allow storage and processing of dynamically produced data and/or signals.

Although numerous embodiments of this invention have been described above with a certain degree of particularity, those skilled in the art could make numerous alterations to the disclosed embodiments without departing from the spirit or scope of this invention. All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A device for allowing a user to control an electro-anatomic mapping system, comprising:
   an electronic control unit;
   input means executing on said electronic control unit for acquiring a user input with respect to a view of an anatomical model of at least a portion of a body of a patient produced by the mapping system, wherein said model comprises a three-dimensional geometry of an anatomical feature of said portion of said body, said user input comprising a user multi-touch, said electronic control unit being configured to communicate said acquired input to the mapping system, wherein said input means includes a touch-responsive display panel coupled to said electronic control unit and further including user interface logic stored in a memory configured to be executed by said electronic control unit, said user interface logic configured to display on said panel a user interface, said user interface logic being further configured to allow a user to interact with the touch-responsive panel and acquire said input from the user, wherein said user interface logic is configured to produce a joystick object on the touch-responsive display panel, said joystick object being configured to detect a direction input with at least respect to said view of said model, wherein said joystick object is further configured to detect a magnitude input with at least respect to said view of said model, and wherein said joystick object includes a circle having a center and a perimeter, said magnitude input corresponding to a distance from said center toward said perimeter at which the user touches said touch-responsive display panel.

2. The device of claim 1, wherein said acquired user input corresponds to at least one of:
   creating a map with respect to said view;
   collecting points with respect to said view;
   segmenting regions by anatomy with respect to said view;
   rotating said view;
   enlarging or reducing a portion of said view;
   panning said view;
   selecting one of plurality of maps for said view;
   selecting a signal trace for display;
   adjusting a signal amplitude;
   adjusting a sweep speed;
   recording a segment;
   placing an event marker;
   placing a lesion marker with respect to said view;
   activating a replay feature of a stored, temporally varying physiologic parameter;
   activating a replay of a stored video clip.

3. The device of claim 1 wherein the mapping system is one of a plurality of electrophysiological diagnostic and therapeutic systems, said user interface logic being configured to selectively present a respective user interface to enable access to and control of one of said electrophysiological systems.

4. The device of claim 3 wherein said user interface logic is further configured to switch between respective user interfaces via a common interface displayed on said touch-responsive display panel.

5. The device of claim 3 wherein said user interface logic is further configured to allow the user to control a plurality of said electrophysiological systems through a single input from the user.

6. The device of claim 1 wherein said device communicates said acquired user input wirelessly.

7. The device of claim 1 further including voice recognition logic stored in said memory and configured to analyze speech input from the user and determine a command for the mapping system.

8. The device of claim 7 wherein said user interface logic is configured to allow the user to enable or disable the operation of the voice recognition logic.

9. A device for allowing a user to control an electro-anatomic mapping system, comprising:
an electronic control unit;
input means executing on said electronic control unit for acquiring a user input with respect to a view of an anatomical model of at least a portion of a body of a patient produced by the mapping system, said user input comprising a user touch, said electronic control unit being configured to communicate said acquired input to the mapping system, wherein said input means includes a touch-responsive display panel coupled to said electronic control unit and further including user interface logic stored in a memory configured to be executed by said electronic control unit, said user interface logic configured to display on said panel a user interface, said user interface logic being further configured to allow a user to interact with the touch-responsive panel and acquire said input from the user, wherein said user interface logic is configured to produce a joystick object on the touch-responsive display panel, said joystick object being configured to detect a direction input with at least respect to said view of said model, wherein said joystick object is further configured to detect a magnitude input with at least respect to said view of said model, and wherein said joystick object includes a circle having a center and a perimeter, said magnitude input corresponding to a distance from said center toward said perimeter at which the user touches said touch-responsive display panel.

10. The device of claim 9 wherein said magnitude input adjusts an acceleration of said view of said model or a cursor.

11. The device of claim 9 wherein said view is displayed on a monitor different from said touch-responsive display panel.

12. The device of claim 9 wherein said user input logic is configured to allow the user to set the mapping system in a follow-me mode wherein the user input is used to control rotation of the view of the model while a representation of a catheter with respect to said view is stationary.

13. The device of claim 9, wherein said model further comprises a map of an electrophysiological parameter.

14. The device of claim 13 wherein said model comprising a three-dimensional geometry of an anatomical feature or said map is from an imaging system wherein said imaging system comprises one of a fluoroscopic system and an ultrasound imaging system using an intra-cardiac echocardiography catheter.

15. The device of claim 9, wherein said acquired user input corresponds to at least one of:
creating a map with respect to said view;
collecting points with respect to said view;
segmenting regions by anatomy with respect to said view;
rotating said view;
enlarging or reducing a portion of said view;
panning said view;
selecting one of plurality of maps for said view;
selecting a signal trace for display;
adjusting a signal amplitude;
adjusting a sweep speed;
recording a segment;
placing an event marker;
placing a lesion marker with respect to said view;
activating a replay feature of a stored, temporally varying physiologic parameter;
activating a replay of a stored video clip.

16. The device of claim 9 wherein the mapping system is one of a plurality of electrophysiological diagnostic and therapeutic systems, said user interface logic being configured to selectively present a respective user interface to enable access to and control of one of said electrophysiological systems.

17. The device of claim 16 wherein said user interface logic is further configured to switch between respective user interfaces via a common interface displayed on said touch-responsive display panel.

18. The device of claim 16 wherein said user interface logic is further configured to allow the user to control a plurality of said electrophysiological systems through a single input from the user.

19. The device of claim 9 wherein said device communicates said acquired user input wirelessly.

20. The device of claim 9 further including voice recognition logic stored in said memory and configured to analyze speech input from the user and determine a command for the mapping system.

21. The device of claim 20 wherein said user interface logic is configured to allow the user to enable or disable the operation of the voice recognition logic.

22. A device for allowing a user to control an electro-anatomic mapping system, comprising:
an electronic control unit;
a computer-readable memory coupled to said electronic control unit;
a touch-responsive display panel coupled to said electronic control unit; and
user interface logic stored in said memory configured to be executed by said electronic control unit, said user interface logic configured to display on said panel a user interface, said user interface logic being further configured to allow a user to interact with the touch-responsive panel and acquire a user input from the user with respect to a view of an anatomical model of at least a portion of a body of a patient produced by the mapping system, wherein said model comprises a three-dimensional geometry of an anatomical feature of said portion of said body, said electronic control unit being configured to communicate said acquired user input to the mapping system, wherein said user interface logic is configured to produce a joystick object on the touch-responsive display panel, said joystick object being configured to detect a direction input with at least respect to said view of said model, wherein said joystick object is further configured to detect a magnitude input with at least respect to said view of said model, and wherein said joystick object includes a circle having a center and a perimeter, said magnitude input corresponding to a distance from said center toward said perimeter at which the user touches said touch-responsive display panel.

* * * * *